United States Patent [19]

Friden

[11] Patent Number: 5,527,527

[45] Date of Patent: * Jun. 18, 1996

[54] TRANSFERRIN RECEPTOR SPECIFIC ANTIBODY-NEUROPHARMACEUTICAL AGENT CONJUGATES

[75] Inventor: Phillip M. Friden, Bedford, Mass.

[73] Assignee: Alkermes, Inc., Cambridge, Mass.

[*] Notice: The portion of the term of this patent subsequent to Oct. 13, 2009, has been disclaimed.

[21] Appl. No.: 4,986

[22] Filed: Jan. 15, 1993

Related U.S. Application Data

[63] Continuation-in-part of Ser. No. 846,830, filed as PCT/US90/05077, Sep. 7, 1990, No. 5,182,107, which is a continuation-in-part of Ser. No. 404,089, Sep. 7, 1989, Pat. No. 5,154,924.

[51] Int. Cl.$^6$ .......................... A61K 39/44; C07K 14/48; C07K 16/46; C07K 17/02
[52] U.S. Cl. .................................. 424/178.1; 530/391.1; 530/391.7; 530/399
[58] Field of Search .................... 530/391.1, 391.7, 530/399, 394, 359, 303, 315, 388, 389; 514/3, 8, 12, 21, 7; 424/85.91, 178.1

[56] References Cited

U.S. PATENT DOCUMENTS

| | | | |
|---|---|---|---|
| 4,292,425 | 9/1981 | Buckler et al. | 536/17.9 |
| 4,434,156 | 2/1984 | Trowbridge | 424/85.8 |
| 4,444,744 | 4/1984 | Goldenberg | 424/1.1 |
| 4,545,985 | 10/1985 | Pastan et al. | 424/85.91 |
| 4,569,789 | 2/1986 | Blattler et al. | 530/391.9 |
| 4,626,507 | 12/1986 | Trowbridge et al. | 435/240.7 |
| 4,631,190 | 12/1986 | Shen et al. | 424/85 |
| 4,801,575 | 1/1989 | Pardridge | 514/4 |
| 4,886,780 | 12/1989 | Faulk | 514/8 |

(List continued on next page.)

FOREIGN PATENT DOCUMENTS

| | | |
|---|---|---|
| 0094844 | 11/1983 | European Pat. Off. . |
| 0175560 | 3/1986 | European Pat. Off. . |
| 0253202 | 1/1988 | European Pat. Off. . |
| 0286418 | 10/1988 | European Pat. Off. . |
| 0286441 | 10/1988 | European Pat. Off. . |
| 0305967 | 3/1989 | European Pat. Off. . |
| 0324625 | 7/1989 | European Pat. Off. . |
| 0327169 | 8/1989 | European Pat. Off. . |
| 0328147 | 8/1989 | European Pat. Off. . |
| 0336383 | 10/1989 | European Pat. Off. . |
| 1564666 | 4/1980 | United Kingdom . |
| WO86/01409 | 3/1986 | WIPO . |
| WO88/07365 | 10/1988 | WIPO . |
| 91/04753 | 4/1991 | WIPO . |
| 91/09965 | 7/1991 | WIPO . |
| 92/13570 | 8/1992 | WIPO . |

OTHER PUBLICATIONS

Grog et al (1983) Proc. Natl. Acad. sci USA 80:6819–6823.
Batra et al (1989) Proc. Natl. Acad. Sci. USA 86:8545–8549.
Batra et al (1991) Mal. Cellular Biol. 11 (4): 2200–2205.
Jeffries et al (1985) Immunology 54:333–341.
Iunard et al (1990) Exp. Neurology 110:25–38.
Olsoneral (1992) J. Neural Tranan. (P–D Sect) 4:79–95.
Eriksdotter–Nilssoneral (1989) Neuroscience 30 (3):755–66
Kordower et al (1994) Proc. Natl. Acad. Sci USA 91:9077–9080.
Trowbridge, I. S. et al., "Anti–Transferrin Receptor Monoclonal Antibody and Toxin–Antibody Conjugates Affect

*Primary Examiner*—Kay K. A. Kim
*Attorney, Agent, or Firm*—Hamilton, Brook, Smith & Reynolds

[57] ABSTRACT

The present invention pertains to a method for delivering a neuropharmaceutical or diagnostic agent across the blood brain barrier to the brain of a host. The method comprises administering to the host a therapeutically effective amount of an antibody-neuropharmaceutical or diagnostic agent conjugate wherein the antibody is reactive with a transferrin receptor. Other aspects of this invention include a delivery system comprising an antibody reactive with a transferrin receptor linked to a neuropharmaceutical or diagnostic agent and methods for treating hosts afflicted with a disease associated with a neurological disorder.

9 Claims, 9 Drawing Sheets

Intraocular Implant Study

U.S. PATENT DOCUMENTS

| | | | |
|---|---|---|---|
| 4,892,827 | 1/1990 | Pastan et al. | 435/193 |
| 4,902,505 | 2/1990 | Pardridge | 424/85.7 |
| 4,992,255 | 2/1991 | Pardridge | 424/1.1 |
| 5,004,697 | 4/1991 | Pardridge | 436/547 |
| 5,087,616 | 2/1992 | Meyers et al. | 514/21 |
| 5,108,987 | 4/1992 | Faulk | 574/8 |
| 5,130,129 | 7/1992 | Pardridge | 424/85.8 |
| 5,154,924 | 10/1992 | Friden | 424/85.91 |
| 5,182,107 | 1/1993 | Friden | 424/85.91 |

OTHER PUBLICATIONS

Growth of Human Tumour Cells", *Nature*, 294 (12): 171–173 (Nov. 1981).

Domingo, D. L. et al., "Transferrin Receptor as a Target for Antibody–Drug Conjugates", *Methods in Enzymology*, 112: 238–247 (1985).

Zovickian, J. et al., "Potent and Specific Killing of Human Malignant Brain Tumor Cells by an Anti–Transferrin Receptor Antibody–Ricin Immunotoxin", *J. Neurosurg.*, 66: 850–861 (1987).

Jeffries, W. A. et al., "Transferrin Receptor on Endothelium of Brain Capillaries", *Nature*, 312(8): 162–163 (1984).

Raso, V. et al., "Monensin is Obligatory for the Cytotoxic Action of a Disulfide Linked Methotrexate–Anti–Transferrin Receptor Conjugate", *Biochem. Biophy. Res. Comm.*, 150(1): 104–110 (1988).

Bjorn, M. J. et al., "Immunotoxins to the Murine Transferrin Receptor: Intracavitary Therapy of mice Bearing Syngeneic Peritoneal Tumors" *Cancer Research* 47 (24, Pt.1): 6639–6645 Dec. 15, 1987).

Smyth, M. J. et al., "The Mode of Action of Methotrexate–Monoclonal Antibody Conjugates" *Immunol. Cell. Biol.*, 65(2): 189–200 (1987).

Pardridge, W. M. "Receptor–Mediated Peptide Transport through the Blood–Brain Barrier", *Endocrine Reviews*, 7(3): 314–330 (1986).

Sutherland, R. et al., "Ubiquitous Cell–Surface Glycoprotein on Tumor Cells is proliferation–Associated Receptor for Transferrin", *Proc. Nat'l Acad. Sci. USA*, 78(7): 4515–4519 (Jul. 1981).

Shen, W.–C. et al., "CIS–Aconityl Spacer Between Daunomycin and Macromolecular Carriers: A Model of Ph–Sensitive Linkage Releasing Drug from a Lysosomotropic Conjugate" *Biochem. and Biophys. Res. Comm. 2(3):* 1048–1054 (Oct. 15, 1981).

Pietersz, G. A. et al., "Novel Synthesis and *in vivo* Characterization of Disulfide–linked Ricin–Monoclonal Antibody Conjugates Devoid of Galactose Binding Activity" *Cancer Res.*, 48: 4469–4476 (1988).

Pietersz, G. A. et al., "The Use of Monoclonal Antibody Conjugates for the Diagnosis and Treatment of Cancer" *Immunol. Cell Biol.*, 65 (Pt. 2): 111–125 (1987).

Gascoigne, N. R. J. et al., "Secretion of a Chimeric T–Cell Receptor–Immunoglobulin Protein" *Proc. Nat'l Acad. Sci. USA* 84: 2936–2940 (1987).

Baldwin, R. W. et al., "Monoclonal Antibodies for Radiommunodetection of Tumours and for Targeting" *Bull. Cancer* (Paris) 70(2): 132–136 (1983).

Byrn, R. A. et al., "Biological Properties of a CD4 Immunoadhesin" *Nature* 344: 667–670 (1990).

Griffin, T. W. et al., "*In Vitro* Cytotoxicity of Recombinant Ricin A Chain–Antitransferrin Receptor Immunotoxin Against Human Adenocarcinomas of Colon and Pancreas" *J. Biol. Res. Mod.*, 7: 559–567 (1988).

Alkan, S. S. et al., "Antiviral and Antiproliferative Effects of Interferons Delivered via Monoclonal Antibodies" *J. Interferon Res.*, 4(3): 355–363 (1984).

Capon, D. J. et al., "Designing CD4 Immunoadhesins for AIDS Therapy" *Nature* 337: 525–531 (1989).

Dautry–Varsat, A. et al., "pH and the Recycling of Transferrin During Receptor–mediated Endocytosis" *Proc. Nat'l Acad. Sci. USA* 80; 2258–2262 (Apr. 1983).

Fishman, J. B. et al., "Receptor–Mediated Transcytosis of Transferrin Across the Blood–Brain Barrier" *J. Neur. Res., 18:* 299–304 (1987).

Pardridge, W. M. et al., "Selective Transport of an Anti–transferrin Receptor Antibody through the Blood–Brain Barrier in vivo" *J. Pharmacol. and Exp. Therapeutics* 259 (1): 66–70 (1991).

Morrison, S. L. et al., "Genetically Engineered Antibody Molecules: New Tools for Cancer Therapy" *Cancer Investigation 6 (2):* 185–192 (1988).

5,527,527

TRANSFERRIN RECEPTOR SPECIFIC ANTIBODY-NEUROPHARMACEUTICAL AGENT CONJUGATES

DESCRIPTION

RELATED APPLICATIONS

This application is a Continuation-in-Part of U.S. application Ser. No. 07/846,830 filed Mar. 6, 1992, now U.S. Pat. No. 5,182,107, which is a Continuation-in-Part of PCT/US90/05077, filed Sep. 7, 1990, designating the United States which, in turn, is a Continuation-in-Part of U.S. application Ser. No. 07/404,089 filed Sep. 7, 1989, now U.S. Pat. No. 5,154,924.

BACKGROUND

The capillaries that supply blood to the tissues of the brain constitute the blood brain barrier (Goldstein et al. (1986) *Scientific American* 255:74–83; Pardridge, W. M. (1986) *Endocrin. Rev.* 7:314–330). The endothelial cells which form the brain capillaries are different from those found in other tissues in the body. Brain capillary endothelial cells are joined together by tight intercellular junctions which form a continuous wall against the passive movement of substances from the blood to the brain. These cells are also different in that they have few pinocytic vesicles which in other tissues allow somewhat unselective transport across the capillary wall. Also lacking are continuous gaps or channels running through the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al, cited supra). If the brain were not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated receptors which, upon binding of their respective ligand, are internalized by the cell (Pardridge, W. M., cited supra). Vesicles containing the receptor-ligand complex then migrate to the abluminal surface of the endothelial cell where the ligand is released.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al, cited supra; Pardridge, W. M., cited supra). Some drugs can be modified to make them more lipophilic and thereby increase their ability to cross the blood brain barrier. However, each modification has to be tested individually on each drug and the modification can alter the activity of the drug. The modification can also have a very general effect in that it will increase the ability of the compound to cross all cellular membranes, not only those of brain capillary endothelial cells.

SUMMARY OF THE INVENTION

The present invention pertains to a method for delivering a neuropharmaceutical or diagnostic agent across the blood brain barrier to the brain of a host. The method comprises administering to the host a therapeutically effective amount of an antibody-neuropharmaceutical or diagnostic agent conjugate wherein the antibody is reactive with a transferrin receptor. The conjugate is administered under conditions whereby binding of the antibody to a transferrin receptor on a brain capillary endothelial cell occurs and the neuropharmaceutical agent is transferred across the blood brain barrier in a pharmaceutically active form. Other aspects of this invention include a delivery system comprising an antibody reactive with a transferrin receptor linked to a neuropharmaceutical agent and methods for treating hosts afflicted with a disease associated with a neurological disorder.

Presently available means for delivering therapeutic or diagnostic agents to the brain are limited in that they are invasive. The delivery system of the present invention is non-invasive and can utilize readily available antibodies reactive with a transferrin receptor as carriers for neuropharmaceutical agents. The delivery system is advantageous in that the antibodies are capable of transporting neuropharmaceutical agents across the blood brain barrier without being susceptible to premature release of the neuropharmaceutical agent prior to reaching the brain-side of the blood brain barrier. Further, if the therapeutic activity of the agent to be delivered to the brain is not altered by the addition of a linker, a noncleavable linker can be used to link the neuropharmaceutical agent to the antibody.

DETAILED DESCRIPTION

Figure 1:
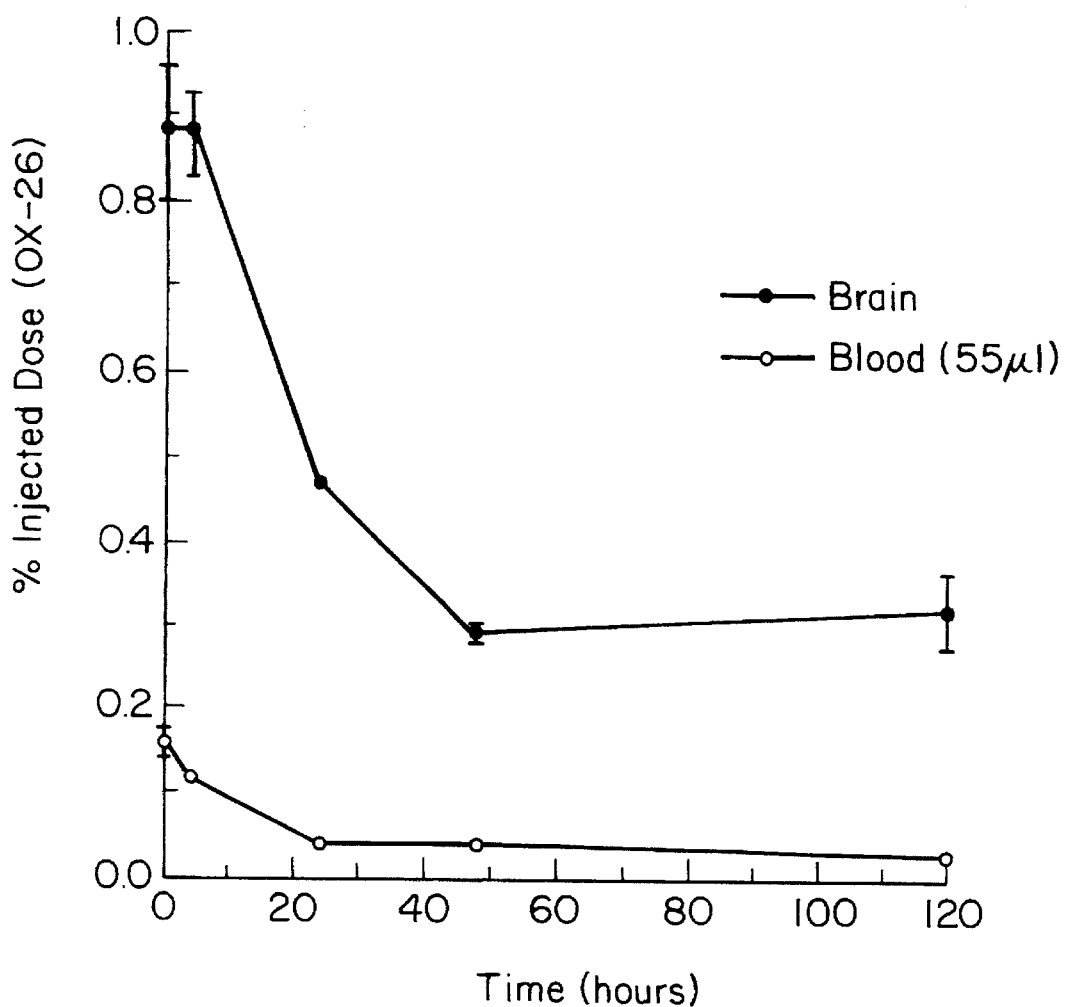
FIG. 1 is a graphic representation of rat brain uptake of $^{14}$C-labelled murine monoclonal antibody (OX-26) to rat transferrin receptor in rats where the percent injected dose of radiolabelled antibody per brain and per 55 µl of blood is plotted versus time post-injection.

The method for delivering a neuropharmaceutical agent across the blood brain barrier to the brain of a host comprises administering to the host a therapeutically effective amount of an antibody-neuropharmaceutical agent conjugate wherein the antibody is reactive with a transferrin receptor present on a brain capillary endothelial cell. The method is conducted under conditions whereby the antibody binds to the transferrin receptor on the brain capillary endothelial cell and the neuropharmaceutical agent is transferred across the blood brain barrier in a pharmaceutically active form.

The host can be an animal susceptible to a neurological disorder (i.e., an animal having a brain). Examples of hosts include mammals such as humans, domestic animals (e.g., dog, cat, cow or horse), mice and rats.

The neuropharmaceutical agent can be an agent having a therapeutic or prophylactic effect on a neurological disorder or any condition which affects biological functioning of the central nervous system. Examples of neurological disorders include cancer (e.g. brain tumors), Autoimmune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents which can be used in this invention include proteins, antibiotics, adrenergic agents, anticonvulsants, small molecules, nucleotide analogs, chemotherapeutic agents, anti-trauma agents, peptides and other classes of agents used to treat or prevent a neurological disorder. Examples of proteins include CD4 and superoxide dismutase (including soluble portions thereof), growth factors (e.g. nerve growth factor (NGF), brain-derived neurotrophic factor (BDNF), ciliary neurotrophic factor (CNTF), neurotrophins 3,4 and 5 (NT-3, 4 and 5) or fibroblast growth factor (FGF)), lymphokines or cytokines (e.g. interferon or interleukins (IL-2)) or antagonists thereof, neurotrophic factors, dopamine decarboxylase and tricosanthin. A neurotrophic factor is defined as a factor capable of maintaining neuron survival or neuron regeneration or differentiation. The properties of the neurotrophic factors are incorporated by reference herein from the following references: (1) for ciliary neurotrophic factor (CNTF), see Manthorpe et al. (1986), *Brain Research,* 367: 282–286; Lin et al. (1989), *Science* 246: 1023–1025; Stockli et al. (1989), *Nature* 342: 920–923; and Lam et al. (1991), *Gene,* 102: 271–276; (2) for brain-derived neurotrophic factor (BDNF), see Barde et al (1987), *Prog. Brain Res.* 71: 185–189; Hofer et al. (1988), *Nature* 331: 261–262; and Leibrock et al (1989), *Nature* 334: 149–152; (3) for neurotrophin 3 (NT-3), see Hohn et al. (1990), *Nature* 344: 339–341; Maisonpierre et al (1990), *Science* 247: 1446–1451; Rosenthal et al (1990), *Neuron* 4: 767–773; Ernfors et al. (1990), *Proc. Natl. Acado Sci. USA* 87: 5454–5458; Jones et al., (1990), *Proc. Natl. Acad. Sci. USA* 87: 8060–8064; and Kaisho et al (1990), *FEBS Lett.* 266, 187–191; (4) for neurotrophin 4 (NT-4), see Hallbook et al (1991), *Neuron* 6: 845–858; and (5) for neurotrophin 5 (NT-5), see Berkemeier et al (1991), *Neuron* 7: 857–866. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides would be somatostatin analogues and enkephalinase inhibitors. Nucleotide analogs which can be used include azidothymidine (hereinafter AZT), dideoxyinosine (ddI) and dideoxycytodine (ddC).

The antibody, which is reactive with a transferrin receptor present on a brain capillary endothelial cell, may also be conjugated to a diagnostic agent. In this method and delivery system, the neuropharmaceutical agent of the neuropharmaceutical agent—anti-transferrin receptor conjugate has been replaced with a diagnostic agent. The diagnostic agent is then delivered across the blood brain barrier to the brain of the host. The diagnostic agent is then detected as indicative of the presence of a physiological condition for which the diagnostic agent is intended. For example, the diagnostic agent may be an antibody to amyloid plaques. When conjugated to an antibody reactive with a transferrin receptor present on a brain capillary endothelial cell, this diagnostic agent antibody can be transferred across the blood brain barrier and can then subsequently immunoreact with amyloid plaques. Such an immunoreaction is indicative of Alzheimer's Disease.

Serum transferrin is a monomeric glycoprotein with a molecular weight of 80,000 daltons that binds iron in the circulation and transports it to the various tissues(Aisen et al. (1980) *Ann. Rev. Biochem.* 49:357–393; MacGillivray et al. (1981) *J. Biol. Chem.* 258:3543–3553). The uptake of iron by individual cells is mediated by the transferrin receptor, an integral membrane glycoprotein consisting of two identical 95,000 dalton subunits that are linked by a disulfide bond. The number of receptors on the surface of a cell appears to correlate with cellular proliferation, with the highest number being on actively growing cells and the lowest being on resting and terminally differentiated cells. Jeffries et al (*Nature Vol.* 312 (November 1984) pp. 167–168) used monoclonal antibodies to show that brain capillary endothelial cells have a high density of transferrin receptors on their cell surface.

Antibodies which can be used within this invention are reactive with a transferrin receptor. The term antibody is intended to encompass both polyclonal and monoclonal antibodies. The preferred antibody is a monoclonal antibody reactive with a transferrin receptor. The term antibody is also intended to encompass mixtures of more than one antibody reactive with a transferrin receptor (e.g., a cocktail of different types of monoclonal antibodies reactive with a transferrin receptor). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to the transferrin receptor to occur.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

The term transferrin receptor is intended to encompass the entire receptor or portions thereof. Portions of the transferrin receptor include those portions sufficient for binding of the receptor to an anti-transferrin receptor antibody to occur.

Monoclonal antibodies reactive with at least a portion of the transferrin receptor can be obtained (e.g., OX-26, B3/25 (Omary et al. (1980) *Nature* 286,888–891), T56/14 (Gatter et al. (1983) *J. Clin. Path.* 36 539–545; Jefferies et al. *Immunology* (1985) 54:333–341), OKT-9 (Sutherland et al. (1981) *Proc. Natl. Acad. Sci. USA* 78:4515–4519), L5.1 (Rovera, C. (1982) *Blood* 59:671–678), 5E-9 (Haynes et al.

(1981) *J. Immunol.* 127:347–351), RI7 217 (Trowbridge et al. *Proc. Natl. Acad. Sci. USA* 78:3039 (1981) and T58/30 (Omary et al. cited supra) or can be produced using somatic cell hybridization techniques (Kohler and Milstein (1975) *Nature* 256, 495–497) or by other techniques. In a typical hybridization procedure, a crude or purified protein or peptide comprising at least a portion of the transferrin receptor can be used as the immunogen. An animal is vaccinated with the immunogen to obtain an anti-transferrin receptor antibody-producing spleen cells. The species of animal immunized will vary depending on the species of monoclonal antibody desired. The antibody producing cell is fused with an immortalizing cell (e.g. myeloma cell) to create a hybridoma capable of secreting anti-transferrin receptor antibodies. The unfused residual antibody-producing cells and immortalizing cells are eliminated. Hybridomas producing the anti-transferrin receptor antibodies are selected using conventional techniques and the selected anti-tranferrin receptor antibody producing hybridomas are cloned and cultured.

Polyclonal antibodies can be prepared by immunizing an animal with a crude or purified protein or peptide comprising at least a portion of a transferrin receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgG, IgM).

The neuropharmaceutical agent can be linked to the antibody using chemical conjugation techniques. Generally, the link is made via an amine or a sulfhydryl group. The link can be a cleavable link or non-cleavable link depending upon whether the neuropharmaceutical agent is more effective when released in its native form or whether the pharmaceutical activity of the agent can be maintained while linked to the antibody. The determination of whether to use a cleavable or non-cleavable linker can be made without undue experimentation by measuring the activity of the drug in both native and linked forms or for some drugs can be determined based on known activities of the drug in both the native and linked form.

For some cases involving the delivery of proteins or peptides to the brain, release of the free protein or peptide may not be necessary if the biologically active portion of the protein or peptide is uneffected by the link. As a result, antibody-protein or antibody peptide conjugates can be constructed using noncleavable linkers. Examples of such proteins or peptides include CD4, superoxide dismutase, interferon, nerve growth factor, tricosanthin, dopamine decarboxylase, somatostatin analogues and enkephalinase inhibitors. Terms such as "CD4" are used herein to include modified versions of the natural molecule, such as soluble CD4, truncated CD4, etc. Examples of non-cleavable linker systems which can be used in this invention include the carbodiimide (EDC), the sulfhydryl-maleimide, and the periodate systems. In the carbodiimide system, a water soluble carbodiimide reacts with carboxylic acid groups on proteins and activates the carboxyl group. The carboxyl group is coupled to an amino group of the second protein. The result of this reaction is a noncleavable amide bond between two proteins.

In the sulfhydryl-maleimide system, a sulfhydryl group is introduced onto an amine group of one of the proteins using a compound such as Traut's reagent. The other protein is reacted with an NHS ester (such as gamma-maleimidobutyric acid NHS ester (GMBS)) to form a maleimide derivative that is reactive with sulfhydryl groups. The two modified proteins are then reacted to form a covalent linkage that is noncleavable.

Periodate coupling requires the presence of oligosaccharide groups on either the carrier or the protein to be delivered. If these groups are available on the protein to be delivered (as in the case of horseradish peroxidase (HRP)), an active aldehyde is formed on the protein to be delivered which can react with an amino group on the carrier. It is also possible to form active aldehyde groups from the carbohydrate groups present on antibody molecules. These groups can then be reacted with amino groups on the protein to be delivered generating a stable conjugate. Alternatively, the periodate oxidized antibody can be reacted with a hydrazide derivative of a protein to be delivered which will also yield a stable conjugate.

The antibody-protein conjugate can also be produced as a contiguous protein using genetic engineering techniques. Gene constructs can be prepared comprising DNA encoding the anti-transferrin receptor antibody fused to DNA encoding the protein to be delivered across the blood brain barrier. The protein can be expressed as a contiguous molecule containing both an antibody portion and a neuropharmaceutical agent portion.

Alternatively, the variable region of the antibody can be conjugated to proteins, such as factors, that can act as neuropharmaceutical agents. Since the variable region of antibodies immunologically interacts with the complementary antigen, here the transferrin receptor, these conjugates can be quickly delivered across the blood brain barrier. This rapid delivery occurs because the conjugates are less bulky than when the constant region of the antibody is present.

Cleavable linkers can be used to link neuro-pharmaceutical agents which are to be deposited in the brain or when a non-cleavable linker alters the activity of a neuropharmaceutical agent. Examples of cleavable linkers include the acid labile linkers described in copending patent application Ser. No. 07/308,960 filed Feb. 6, 1989, the contents of which are hereby incorporated by reference. Acid labile linkers include disulfides such as N-succinimidyl-3-(2-pyridyldithio) propionate (SPDP; Pharmacia), cis-aconitic acid, cis-carboxylic alkadienes, cis-carboxylic alkatrienes, and poly-maleic anhydrides. Other cleavable linkers are linkers capable of attaching to primary alcohol groups. Examples of neuropharmaceutical agents which can be linked via a cleavable link include AZT, ddI, ddC, adriamycin, amphotericin B, pyrimethamine, valproate, methotrexate, cyclophosphamide, carboplatin and superoxide dimutase. The noncleavable linkers used generally to link proteins to the antibody can also be used to link other neuropharmaceutical agents to the antibody.

SPDP is a heterobifunctional crosslinking reagent that introduces thiol-reactive groups into either the monoclonal antibody or the neuropharmaceutical agent. The thiol-reactive group reacts with a free sulfhydryl group forming a disulfide bond.

In addition to covalent binding, conjugates can be formed employing non-covalent bonds, such as those formed with bifunctional antibodies, ionic bonds, hydrogen bonds, hydropholic interactions, etc. The important consideration is that the conjugate bond be strong enough to result in passage of the conjugate through the blood-brain barrier.

The antibody-neuropharmaceutical agent conjugates can be administered orally, by subcutaneous or other injection, intravenously, intramuscularly, parenternally, transdermally, nasally or rectally. The form in which the conjugate is administered (e.g., capsule, tablet, solution, emulsion) will depend at least in part on the route by which it is administered.

A therapeutically effective amount of an antibody-neuropharmaceutical agent conjugate is that amount necessary to significantly reduce or eliminate symptoms associated with a particular neurological disorder. The therapeutically effective amount will be determined on an individual basis and will be based, at least in part, on consideration of the individuals's size, the severity of symptoms to be treated, the result sought, the specific antibody, etc. Thus, the therapeutically effective amount can be determined by one of ordinary skill in the art employing such factors and using no more than routine experimentation.

Although the description above focuses on antibodies, any protein which interacts with the extracellular domain of the transferrin receptor, including the ligand binding site, could potentially serve as a vehicle for the delivery of drugs across the blood-brain barrier. In addition to anti-transferrin receptor antibodies, this would include transferrin, the ligand which binds to the receptor, and any transferrin derivatives which retain receptor-binding activity. In fact, any ligand which binds to the transferrin receptor could potentially be employed.

Conjugates between ligands and therapeutic or diagnostic agents can also be prepared where the ligands are reactive with other receptors, besides the transferrin receptor, which can also mediate the endocytotic or transcytotic process of transporting macromolecules across the blood-brain barrier. These receptors are also on the cell surface of the endothelial cells which line brain capillaries. Among the receptor types are those that react with insulin-like growth factors 1 or 2 (IGF 1 or 2) or insulin itself. Other receptor types are those that react with low density lipoprotein or with vasopressin. The ligands are those substances which usually react with these receptors (e.g. IGF 1, IGF 2 or insulin, low density liproprotein or vasopressin), derivatives of these substances which retain receptor-binding activity or antibodies to these receptors. The properties of transferrin and other ligands which bind to receptors on the cell surface of brain capillary endothelial cells are incorporated by reference herein from the following references: (1) for transferrin, see Omary et al. (1981), *J. Biol. Chem.* 256: 12888–12895; and McClelland et al. (1984), *Cell* 39: 267–274; (2) for insulin, see Pardridge et al. (1985), *J. Neurochem.* 44: 1771–1778; (3) for insulin-like growth factors, see Duffy et al. (1988), *Metabolism* 37: 136–140; and Rosenfeld et al. (1987), *Biochem. Biophys. Res. Comm.* 149: 159–166; (4) for low density lipoprotein, see Meresse et al. (1989), *J. Neurochem.* 53: 340–345; (5) and for vasopressin, see Zlokovic et al. (1990), *Biochem. Biophys ACTA* 1025: 191–198; Zlokovic et al. (1991), *Am. J. Physiol.* 260: F216–F224; and Zlokovic et al. (1991), *Am. J. Physiol.* 260: E633–E640. The therapeutic or diagnostic agents which can be conjugated to the ligands include the above-mentioned proteins such as nerve growth factor, superoxide dismutase, CD-4 or anti-amyloid antibody and drugs such as adriamycin, methotrexate or AZT.

The present invention will be illustrated by the following examples:

EXAMPLE 1

In Vitro Binding of Murine Monoclonal Antibodies to Human Brain Endothelial Cells Two murine monoclonal antibodies, B3/25 and T58/30, described by Trowbridge (U.S. Pat. No. 4,434,156 issued Feb. 28, 1984, and *Nature* Vol. 294, pp. 171–173 (1981)), the contents of both are hereby incorporated by reference, which recognize the human transferrin receptor were tested for their ability to bind to human brain capillary endothelial cells. Hybridoma cell lines which produce B3/25 and T58/30 antibodies were obtained from the American Type Culture Collection (ATCC) in Rockville, Md., and grown in DMEM medium supplemented with 2.0 mM glutamine, 10.0 mM HEPES (pH 7.2), 100 µM non-essential amino acids and 10% heat-inactivated fetal calf serum. The hybridoma cultures were scaled-up in 225 cm$^2$ T-flasks for the production of milligram quantities of IgG antibody. The hybridoma supernatants were concentrated 50× using vacuum dialysis and applied to a protein-A sepharose column using the BioRad MAPS buffer system. Purified antibody was eluted from the column, dialyzed against 0.1M sodium phosphate (pH 8.0), concentrated and stored in aliquots at −20° C.

Primary cultures of human brain endothelial cells were grown in flat-bottom 96-well plates until five days post-confluency. The cells were then fixed using 3.0% buffered formalin and the plate blocked with 1.0% bovine serum albumin (BSA) in Dulbecco's phosphate buffered saline (DPBS). Aliquots (100 µl) of the B3/25 or T58/30 antibodies, either in the form of culture supernatants or purified protein, were then added to the wells (antibody concentrations were in the range of 1–50 µg/ml). Antibody which had specifically bound to the fixed cells was detected using a biotin-labeled polyclonal goat-anti-mouse IgG antisera followed by a biotinylated horseradish peroxidase (HRP)/ avidin mixture (Avidin Biotin Complex technique). Positive wells were determined using a Titertek Multiscan Enzyme Linked Immunosorbent Assay (ELISA) plate reader. The results showed that both antibodies bind to human brain capillary endothelial cells with the T58/30 antibody exhibiting a higher level of binding.

These same antibodies were also tested for binding to human brain capillaries using sections of human brain tissue that were fresh frozen (without fixation), sectioned on a cryostat (section thickness was 5–20 µm), placed on glass slides and fixed in acetone (10 minutes at room temperature). These sections were then stored at −20° C. prior to use.

The slides containing the human brain sections were allowed to come to room temperature prior to use. The sections were then rehydrated in DPBS and incubated in methanol containing 0.3% H$_2$O$_2$ to block endogenous peroxidate activity. The sections were blocked for fifteen minutes in a solution containing 0.2% non-fat dry milk and 0.2% methylmannopyranoside. B3/25 and T58/30 antibodies, purified as discussed above, were applied to the sections at a concentration of 5–50 µg/ml and incubated at room temperature for one to two hours. Antibody that specifically bound to the tissue was detected using the Avidin-Biotin Complex (ABC) technique as described above for the ELISA assay. Staining of capillaries in the human brain sections was observed with both the B3/25 and T58/30 antibodies. The T58/30 antibody also displayed some binding to the white matter of the brain cortex.

EXAMPLE 2

In-Vitro Binding of Murine Monoclonal Antibody OX-26 to Rat Transferrin Receptor The OX-26 murine antibody, which recognizes the rat transferrin receptor, has been shown in vivo to bind to brain capillary endothelial cells (Jeffries et al., cited supra). The murine hybridoma line which produces the OX-26 murine antibody was obtained and the hybridoma cell line was grown in RPMI 1640 medium supplemented with 2.0 mM glutamine and 10% heat-inactivated fetal calf serum. The OX-26 antibody was purified using the affinity chromatography technique described in Example 1.

The purified antibody was tested in vitro as described for the anti-human transferrin receptor antibodies in Example 1 to determine whether it would bind to brain capillaries in fresh frozen, acetone-fixed rat brain sections. The results showed that the OX-26 anti-transferrin receptor antibody did bind to capillaries in rat brain sections in vitro.

EXAMPLE 3

In-Vivo Binding of OX-26 Murine Monoclonal Antibody to Rat Transferrin Receptor

Dose Range

The anti-rat transferrin receptor antibody OX-26 was tested in vivo by injecting purified antibody (purification as described in Example 1) into female Sprague-Dawley rats (100–150 gm) via the tail vein. Prior to injection, the rats were anesthetized with halothane. The samples, ranging from 2.0 mg to 0.05 mg of antibody/rat were injected into the tail vein in 400 µl aliquots. All doses were tested in duplicate animals. One hour post-injection, the animals were sacrificed and perfused through the heart with DPBS to clear the blood from the organs. Immediately after the perfusion was completed, the brain was removed and quick frozen in liquid nitrogen. The frozen brain was then sectioned (30–50 µm) on a cryostat and the sections placed on glass microscope slides. The brain sections were air dried at room temperature one to two hours before fixation in acetone (10 minutes at room temperature). After this treatment the sections could be stored at −20° C.

The OX-26 antibody was localized in the brain sections using immunohistochemistry as described above for the in vitro experiments in Example 1. The addition of the primary antibody was unnecessary in that it is present in the brain sections. The results indicated that the OX-26 antibody binds to rat brain capillary endothelial cells and that doses of as little as 50 µg result in detectable levels of antibody in the brain using the methods described herein. Doses above 0.5 mg did not appear to show significantly more antibody binding to the endothelial cells, suggesting that the sites for antibody binding may be saturated. No specific binding to capillary endothelium was detected in the liver, kidney, heart, spleen or lung.

A non-specific antibody of the same subclass as OX-26 (IgG 2a) was also tested in vivo to show that the binding of OX-26 to rat brain endothelial cells that has been observed is specific to the OX-26 antibody. 0.5 mg of the control antibody was injected per rat as described above. The results indicate that the staining pattern observed with the OX-26 antibody is specific to that antibody.

Time Course

After establishing that the OX-26 antibody is detectable in the rat brain capillaries after in vivo administration, the time frame in which this binding occurred was determined. Using 0.5 mg of purified OX-26 antibody as the standard dose, brain sections from animals sacrificed 5 minutes, 15 minutes, 1 hour, 2 hours, 4 hours, 8 hours and 24 hours post-injection were examined for the presence of OX-26 antibody. All doses were administered in 400 µl aliquots and each time point was tested in duplicate animals. Samples were injected and the rats were processed at the various times post-injection as described above in the dose range section.

The results showed that the OX-26 antibody can be detected in or on the rat brain capillary endothelial cells as early as five minutes and as late as 24 hours post-injection. At 4 and 8 hours post-injection, the staining pattern of the antibody is very punctate suggesting that the antibody has accumulated in vesicular compartments either in endothelial or perivascular cells.

EXAMPLE 4

The Use of a Conjugate of OX-26 Murine Monoclonal Antibody for Tranferring Horseradish Peroxidase Across the Blood Brain Barrier Horseradish Peroxidase (HRP; 40 kD) was chosen as a compound to be delivered to the brain because it is similar in size to several therapeutic agents and it can be easily detected in the brain using an enzymatic assay. HRP was conjugated to the OX-26 antibody using a non-cleavable periodate linkage and the ability of the antibody to function as a carrier of compounds to the brain was examined. The antibody conjugate was tested in vivo to determine if the antibody could deliver HRP to the brain.

The antibody (10 mg) was first dialyzed overnight against 0.01M sodium bicarbonate (pH 9.0). The HRP (10 mg) was dissolved in 2.5 ml deionized water, 0.1M sodium periodate (160 µl) was added and the mixture was incubated for five minutes at room temperature. Ethylene glycol (250 µl) was added to the HRP solution followed by an additional five minute incubation. This solution was then dialyzed overnight against 1.0 mM sodium acetate buffer (pH 4.4). To the dialyzed OX-26 antibody (2.0 ml, 5.08 mg/ml) was added 200 µl of 1.0M sodium bicarbonate buffer, pH 9.5 and 1.25 ml of the dialyzed HRP solution. This mixture was incubated in the dark for two hours followed by the addition of 100 µl of 10 mg/ml sodium borohydride. The resulting mixture was incubated two additional hours in the dark at 4° C. The protein was precipitated from the solution by the addition of an equal volume of saturated ammonium sulfate and resuspended in a minimal volume of water. Free antibody was removed from the mixture by chromatography on a concanavalin A-sepharose column (a column which binds HRP and the HRP-antibody conjugate and allows the free antibody to pass through). The free HRP was removed by chromatography on a protein A-sepharose column which retains the antibody-HRP conjugate. The final product had an HRP/antibody ratio of 4/1.

A time course experiment identical to that described in Example 3 was performed using the antibody-HRP conjugate. The antibody-HRP conjugate (0.5 mg) was injected in a 400 µl aliquot/rat. The animals were sacrificed at the various times post-injection and the brains processed as described above in Example 3. The antibody HRP conjugate was localized in the brain either by staining for antibody immunohistochemically as described in Example 1 or by directly staining the brain sections for the presence of HRP. To detect HRP, the slides were first allowed to come to room temperature before incubating in methanol for thirty minutes. The brain sections were then washed in DPBS and reacted with 3,3'-diamino benzidine (DAB), the substrate for HRP. The results showed that the OX-26 antibody HRP conjugate binds to rat brain capillary endothelial cells in a manner identical to that of the unconjugated antibody. The punctate staining 4–8 hours after injection which was seen with the antibody alone is also seen with the antibody conjugate, suggesting that the conjugate can also be going into the pericytes on the abluminal side of the blood brain barrier. Taken together, these results indicate that the OX-26 antibody can deliver a protein molecule of at least 40 KD to the brain.

EXAMPLE 5

The In-Vivo Delivery of Adriamycin to the Brain by Murine Monoclonal Antibody OX-26

A non-cleavable linker system similar to that used in Example 4, was used to couple the chemotherapeutic drug adriamycin to the OX-26 antibody. The availability of antibodies that can detect adriamycin, as well as the system previously described in Example 1 for detecting the antibody carrier allowed the use of immunohistochemical techniques for monitoring the localization of the antibody carrier as well as the delivery of adriamycin to the brain.

To conjugate adriamycin to the antibody, the drug (10 mg in 0.5 ml DPBS) was oxidized by the addition of 200 μl of 0.1M sodium periodate. This mixture was incubated for one hour at room temperature in the dark. The reaction was quenched by the addition of 200 μl of ethylene glycol followed by a five minute incubation. The OX-26 antibody (5.0 mg in 0.5 ml of carbonate buffer (pH 9.5)) was added to the oxidized adriamycin and incubated at room temperature for one hour. Sodium borohydride (100 μl of 10 mg/ml) was added and the mixture was incubated for an additional two hours at room temperature. The free adriamycin was separated from the OX-26 antibody-adriamycin conjugate by chromatography on a PD-10 column. The adriamycin/OX-26 antibody ratio within the conjugate was 2/1. for this particular batch of conjugate.

The effectiveness of the OX-26 antibody as a carrier for delivering adriamycin to the brain was determined by administering 0.5 mg of the antibody-adriamycin conjugate in a 400 μl aliquot per rat by injection via the tail vein. One hour post-injection, the rat was sacrificed and the brain processed as described in Example 1. All injections were performed in duplicate. As a control, 400 μg of free adriamycin in a 400 μl aliquot was also injected into a rat. Immunohistochemistry was used to detect both the carrier OX-26 antibody and the adriamycin in the rat brain sections. In the case of adriamycin, polyclonal rabbit anti-adriamycin antisera was applied to the sections followed by a biotinylated goat anti-rabbit IgG antisera. This was then followed by the addition of a biotinylated HRP/avidin mixture and enzymatic detection of HRP.

The results indicate that both the OX-26 antibody and the conjugated adriamycin localized to the rat brain capillary endothelial cells after in vivo administration. There is no evidence that free adriamycin binds to brain capillary endothelial cells or enters the brain.

An adriamycin-OX-26 conjugate coupled via a carbodiimide linkage was also synthesized (drug/ antibody ratio of 10/1) and tested in vivo. The results of this experiment were essentially identical to that obtained with the periodate-linked antibody-drug conjugate. In both cases, staining for the antibody carrier was quite strong and was visualized in the capillaries in all areas of the brain. This staining was evenly distributed along the capillaries. Staining for adriamycin was less intense but again was seen in capillaries throughout the brain. Some punctate staining was observed which suggests accumulation in pericytes which lie on the brain side of the blood-brain barrier.

EXAMPLE 6

In Vivo Delivery of Methotrexate to the Brain by Murine Monoclonal Antibody OX-26.

A noncleavable carbodiimide linkage was used to couple methotrexate to the OX-26 murine monoclonal antibody. A system analogous to that described in Example 5 was used to monitor the delivery of both the methotrexate and the carrier antibody to the brain capillary endothelial cells.

Methotrexate was coupled to murine monoclonal antibody OX-26 via its active ester. Briefly, 81 mg (0.178 mM) of methotrexate (Aldrich) was stirred with 21 mg (0.182 mM) of N-hydroxysuccinimide (Aldrich) in 3 ml of dimethylformamide (DMF) at 4° C. Ethyl-3-dimethylaminopropyl-carbodiimide (180 mg;EDC;0.52mM) was added to this solution and the reaction mixture was stirred overnight. The crude ester was purified from the reaction by-products by flash chromatography over silica gel 60 (Merck) using a solution of 10% methanol in chloroform as an eluant. The purified active ester fractions were pooled and concentrated to dryness. The ester was dissolved in 1 ml of DMF and stored at −20° C. until use. 50 mg (50%) of active ester was recovered as determined by $A_{372}(\epsilon_{b\ 372}=7200)$.

A solution of OX-26 containing 2.1 mg (14 nmoles) of antibody in 0.9 ml of 0.1M phosphate (pH 8.0) was thawed to 4° C. To this stirred antibody solution was added 1.4 μL (140 nmoles) of the active ester prepared as described above. After 16 hours at 4° C., the mixture was chromatographed over Sephadex PD-10 column (Pharmacia) using phosphate buffered saline (PBS) to separate conjugate from free drug. The fractions containing the antibody-methotrexate conjugate were pooled. Antibody and drug concentration were determined spectrophotometrically as described by Endo et al. (*Cancer Research* (1988) 48:3330–3335). The final conjugate contained 7 methotrexates/antibody.

The ability of the OX-26 monoclonal antibody to deliver methotrexate to the rat brain capillary endothelial cells was tested in vivo by injecting 0.2 mg of conjugate (in 400 μl) into each of two rats via the tail vein. The animals were sacrificed one hour post-injection and the brains processed for immunohistochemistry as described in Example 1. To detect methotrexate in the brain, a rabbit antisera raised against methotrexate was used as the primary antibody. A biotinylated goat-anti-rabbit antisera in conjunction with a mixture of biotinylated HRP and avidin was then used to visualize methotrexate in the rat brain. The carrier antibody was detected as described previously.

The results of these experiments indicate that methotrexate in the form of a conjugate with OX-26 does accumulate along or in the capillary endothelial cells of the brain. The staining observed for methotrexate is comparable in intensity to that seen for the carrier. The staining appears to be in all areas of the brain and is evenly distributed along the capillaries.

EXAMPLE 7

Antibody Derivatives

The Fc portion of the OX-26 murine monoclonal antibody was removed to determine whether this would alter its localization to or uptake by the rat brain capillary endothelial cells. Fab fragments were produced from intact IgG's via digestion with papain. F(ab)$_2$ fragments of OX-26 were produced from intact IgG's via digestion with pepsin. Kits available from Pierce Chemical Co. contain the reagents and protocols for cleaving the antibody to obtain the fragments. The F(ab')$_2$ fragment (0.2 mg doses) in 400 µl aliquots were injected into rats via the tail vein. A time course experiment identical to that done with the intact antibody (Example 2) was then performed. F(ab')$_2$ fragment was detected immunohistochemically using a goat anti-mouse F(ab')$_2$ antisera followed by a biotinylated rabbit anti-goat IgG antisera. A biotinylated HRP/avidin mixture was added and the antibody complex was visualized using an HRP enzymatic assay. The results indicate that the F(ab)$_2$ fragment of the OX-26 antibody binds to the capillary endothelial cells of the rat brain.

EXAMPLE 8

Measurement of OX-26 in Brain Tissue

To quantitate the amount of OX-26 which accumulates in the brain, radioactively-labelled antibody was injected into rats via the tail vein. Antibodies were labelled with either $^{14}$C-acetic anhydride or $^3$H-succinimidyl propionate essentially as described in Kummer, U., *Methods in Enzymology*, 121: 670–678 (1986), Mondelaro, R. C., and Rueckert, R. R., *J. of Biological Chemistry*, 250: 1413–1421 (1975), hereby incorporated by reference. For all experiments, the radiolabelled compounds were injected as a 400 µl bolus into the tail vein of female Sprague-Dawley rats (100–125 gms) under Halothane anesthesia and the animals were sacrificed at the appropriate time post-injection using a lethal dose of anesthetic. A $^3$H-labelled IgG2a control antibody was co-injected with the $^{14}$C-labelled OX-26 to serve as a control for non-specific radioactivity in the brain due to residual blood. At the appropriate time post-injection, animals were sacrificed and the brains were removed immediately and homogenized in 5 ml of 0.5% sodium dodecylsulfate using an Omni-mixer. An aliquot of the homogenate was incubated overnight with 2 ml of Soluene 350 tissue solubilizer prior to liquid scintillation counting. All data were collected as disintegrations per minute (dpm). Blood samples were centrifuged to pellet red blood cells (which do not display significant binding of radiolabelled materials) and the radioactivity in an aliquot of serum determined using liquid scintillation counting.

The amount of antibody associated with the brain was determined at various times post-injection to examine the pharmacokinetics of brain uptake. In addition, the amount of labelled antibody in the blood was measured so that the rate of clearance from the bloodstream could be determined. This information was also used to calculate the amount of radioactivity in the brain due to blood contamination, which was then subtracted from the total to give the amount of antibody that is specifically associated with the brain.

A peak level of $^{14}$C-labelled OX-26 corresponding to approximately 0.9% of the injected dose was reached in the brain between 1 and 4 hours post-injection as illustrated in FIG. 1 (with the values shown as means plus or minus standard error of the mean (SEM) and N=3 rats per time point). The amount of radioactivity associated with the brain decreased steadily from 4 to 48 hours post-injection, at which point it leveled off at approximately 0.3% of the injected dose. The accumulation of OX-26 in the brain was significantly reduced by the addition of unlabeled monoclonal antibody (0.5 or 2.0 mg in the bolus injection). As an additional control, a $^3$H-IgG2a control antibody was co-injected with the $^{14}$C-OX-26. The control antibody did not accumulate in the brain and represented the blood contamination of the brain.

In contrast to the levels in the brain, the blood level of OX-26 dropped quite dramatically immediately after injection such that by 1 hour post-injection, the percent of injected dose in 55 µl of blood (the volume of blood associated with the brain) was approximately 0.16% as illustrated in FIG. 1. This corresponds to a value of approximately 20% of the injected dose in the total blood volume of the rat. Extraction of total IgG from serum followed by polyacrylamide gel electrophoresis (PAGE) and autoradiography did not reveal detectable levels of OX-26 degradation indicating that the antibody remains intact in the blood as long as 48 hours after injection.

EXAMPLE 9

Distribution of OX-26 in Brain Parenchyma and Capillaries

To demonstrate that anti-transferrin receptor antibody accumulates in the brain parenchyma, homogenates of brains taken from animals injected with labelled OX-26 were depleted of capillaries by centrifugation through dextran to yield a brain tissue supernatant and a capillary pellet. Capillary depletion experiments followed the procedure of Triguero, et al., *J. of Neurochemistry*, 54: 1882–1888 (1990), hereby incorporated by reference. As for the brain uptake experiments of Example 8, the radiolabelled compounds were injected as a 400 µl bolus into the tail vein of females Sprague-Dawley rats (100–125 gm) under Halothane anesthesia and the animals were sacrificed at the appropriate time post-injection using a lethal dose of anesthetic. A $^3$H-labelled IgG 2a control antibody was co-injected with the $^{14}$C-labelled OX-26 to serve as a control for non-specific radioactivity in the brain due to residual blood. After sacrifice, the brains were removed and kept on ice. After an initial mincing, the brains were homogenized by hand (8–10 strokes) in 3.5 ml of ice cold physiologic buffer (100 mM NaCl, 4.7 mM KCl, 2.5 mM CaCl$_2$, 1.2 mM KH$_2$PO$_4$, 1.2 mM MgSO$_4$, 14.5 mM HEPES, 10 mM D-glucose, pH 7.4). Four ml of 26% dextran solution in buffer was added and homogenization was continued (3 strokes). After removing an aliquot of the homogenate, the remainder was spun at 7200 rpm in a swinging bucket rotor. The resulting supernatant was carefully removed from the capillary pellet. The entire capillary pellet and aliquots of of the homogenate and supernatant were incubated overnight with 2 ml of Soluene 350 prior to liquid scintillation counting. This method removes greater than 90% of the vasculature from the brain homogenate (Triguero et al., cited supra).

Figure 2:
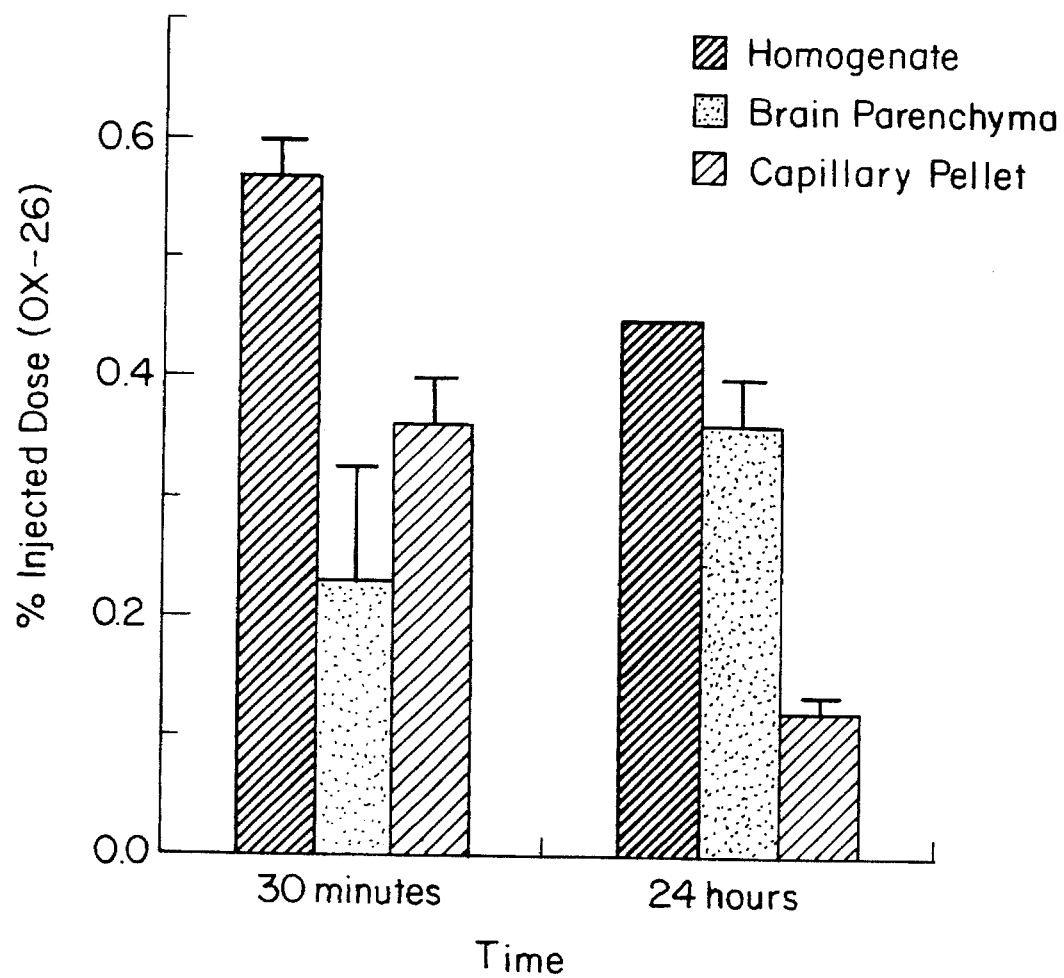
FIG. 2 is a histogram illustrating time dependent changes in the disposition of radiolabelled OX-26 between brain parenchyma and vasculature.

A comparison of the relative amounts of radioactivity in the different brain fractions as a function of time indicates whether transcytosis of the labelled antibody has occurred. The amount of OX-26 in total brain homogenate, the brain parenchyma fraction and the brain capillary fraction at an early time (30 minutes) and a later time (24 hours) post-injection is illustrated in FIG. 2. The values in FIG. 2 are shown as means±SEM with N=3 rats per time point. At the 30 minute time point, more of the radiolabelled antibody is associated with the capillary fraction than with the brain parenchyma fraction (0.36% of the injected dose (%ID) and 0.23% ID, respectively). By 24 hours post-injection, the distribution is reversed and the majority of the radioactivity (0.36% ID) is in the parenchymal fraction as compared to the capillary fraction (0.12% ID). The redistribution of the radiolabelled OX-26 from the capillary fraction to the parenchyma fraction is consistent with the time dependent migration of the anti-transferrin receptor antibody across the blood-brain barrier.

EXAMPLE 10

Figure 3:
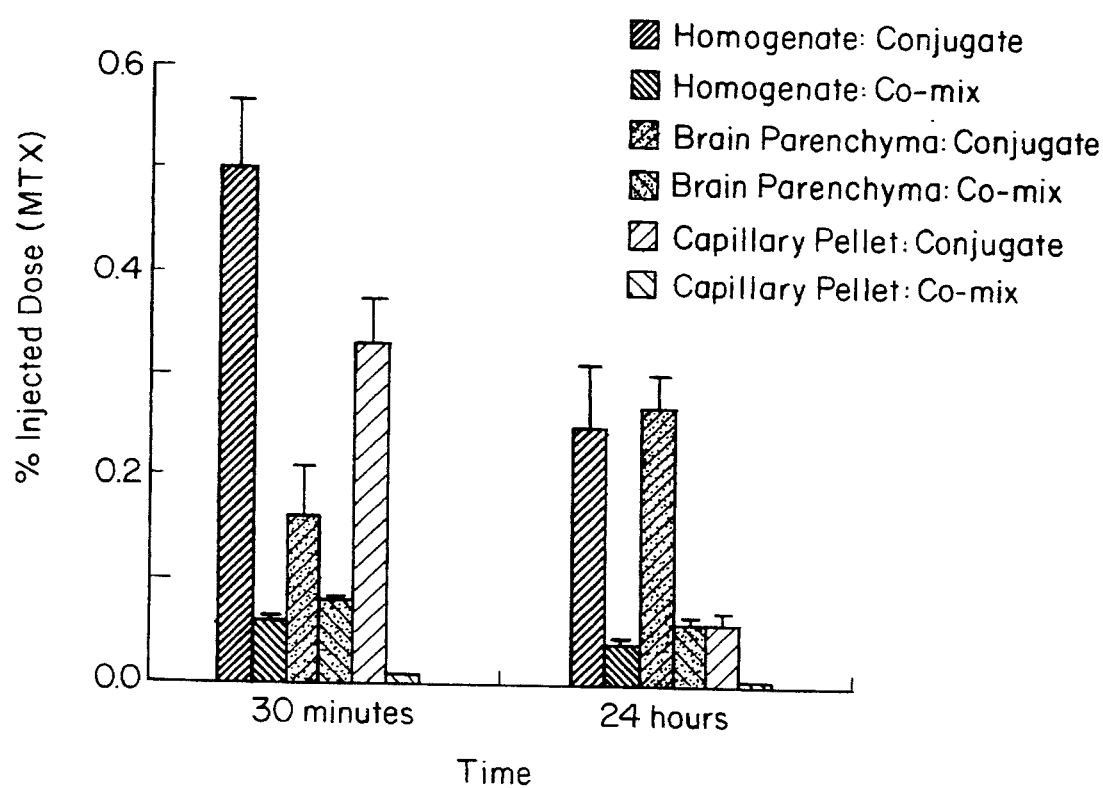
FIG. 3 is a histogram illustrating the enhanced delivery of methotrexate across the blood-brain barrier when administered as a conjugate with OX-26.

Distribution of an OX-26-methotrexate Conjugate in Brain Parenchyma and Capillaries Capillary depletion studies following the procedures described in Example 9 were performed with an OX-26-methotrexate (MTX) conjugate linked via a gamma-hydrazid as described in Kralovec, et al., *J. of Medicinal Chem.*, 32: 2426–2431 (1989), hereby incorporated by reference, in which the MTX moiety was labelled with $^3$H. As with unconjugated antibody, the amount of label in the capillary fraction at 30 minutes post-injection is greater than the parenchyma fraction (approximately 2-fold as illustrated in FIG. 3, with the data expressed as means±SEM and N=3 rats per time point). This distribution changes over time such that by 24 hours post-injection, approximately 4.5-fold more of the labelled MTX is in the brain parenchyma than in the capillaries. These results are consistent with those obtained with unconjugated antibody and, again, suggest that these compounds cross the blood-brain barrier.

To ensure that these results were not due to contaminating amounts of free $^3$H-MTX or $^3$H-MTX that had been cleaved from the conjugate after injection, a co-mix of labelled drug and antibody was injected into rats and a capillary depletion experiment performed. The amount of $^3$H-MTX in the different brain fraction is significantly lower for the co-mix as compared to the conjugate (as much as 47 fold in the case of the capillary fraction at 30 minutes post-injection as illustrated in FIG. 3). The $^3$H-MTX and the co-mix also does not show the change in distribution of the label between the different brain fractions over time as was seen with the antibody-MTX conjugate or antibody alone. These results demonstrate that delivery of $^3$H-MTX across the blood-brain barrier to the brain parenchyma is greatly enhanced by the conjugation of the drug to the anti-transferrin receptor antibody OX-26.

EXAMPLE 11

Distribution of OX-26-AZT in Brain Parenchyma and Capillaries

Capillary depletion studies following the procedures of Example 9 were performed with an OX-26-AZT conjugate using a pH-sensitive succinate linker. These studies employed a dual-labelled conjugate in which the AZT was $^{14}$C-labelled and the antibody carrier was $^3$H-labelled. The use of such a conjugate allowed independent monitoring of the disposition of both the antibody and AZT within the brain.

The linker was synthesized as follows. Succinic anhydride was used to acylate the AZT by reacting equimolar amounts of these two compounds for 3 hours at room temperature under argon in the presence of dimethylaminopyridine and sodium bisulfate in freshly distilled pyridine. The product was isolated by chromatography on a DEAE sephadex A50 column run with a triethylammonium bicarbonate buffer. The succinate derivative of AZT was activated at the carboxyl group as the NHS ester by reaction with equimolar amounts of N-hydroxysuccinimide and dicyclohexylcarbodiimide (DCC) in freshly distilled THF at 4° C. for 2 hours. The product was purified by flash charomatography on silica gel. The resulting NHS-ester of AZT-succinate was used to acylate amine groups on OX-26, resulting in an AZT-OX-26 conjugate. A 15-fold molar excess of AZT-NHS ester was reacted with OX-26 in HEPES buffer overnight at 4° C. The antibody-drug conjugate was isolated from free drug on a PD-10 column. The molar ratio of drug to antibody was 7:1. These studies employed a dual-labelled conjugate in which the AZT was $^{14}$C-labelled and the antibody carrier was $^3$H-labelled.

Figure 4A:
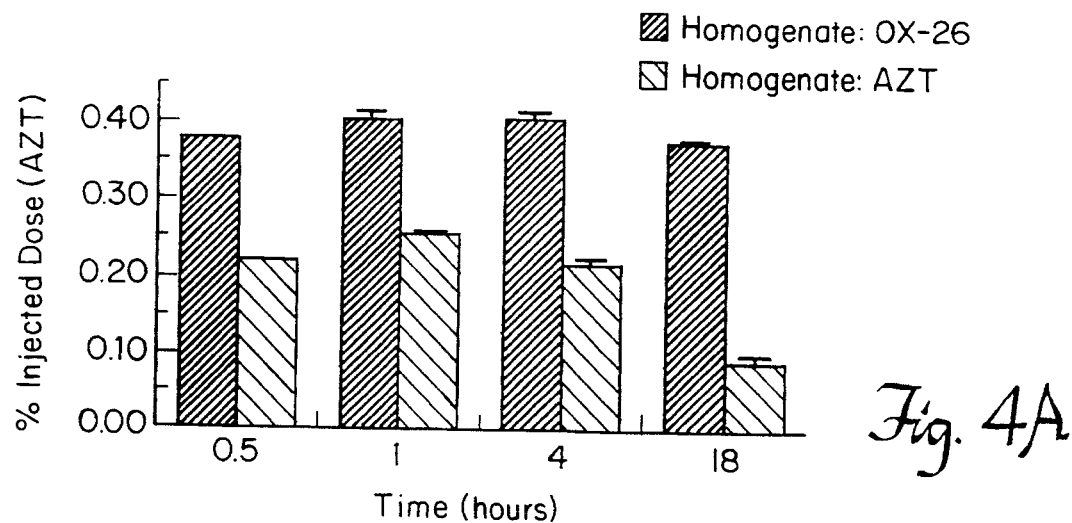
FIGS. 4A–4C illustrate in three histograms (A, B and C) the distribution in the brain of both the antibody and the AZT components of an OX-26-AZT conjugate.
Figure 4B:
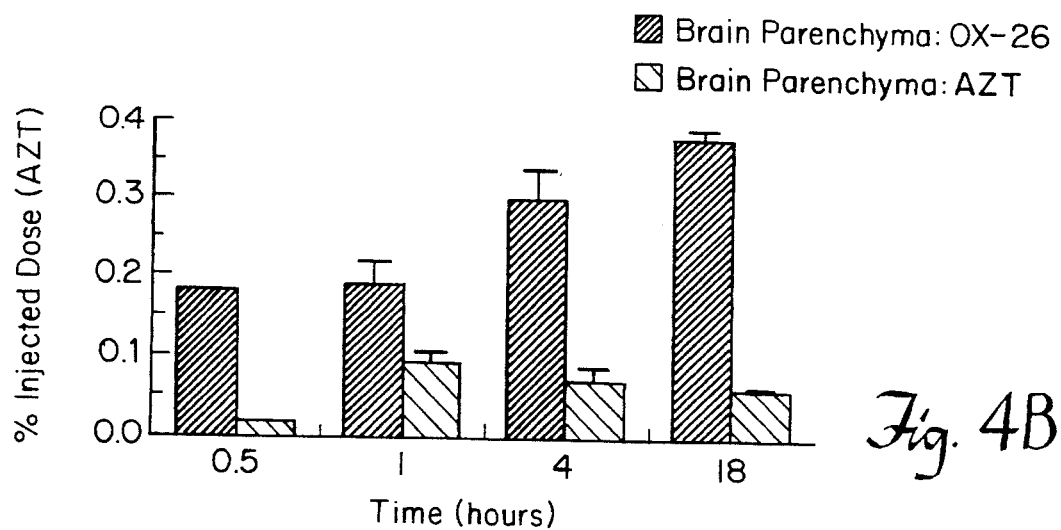
Figure 4C:
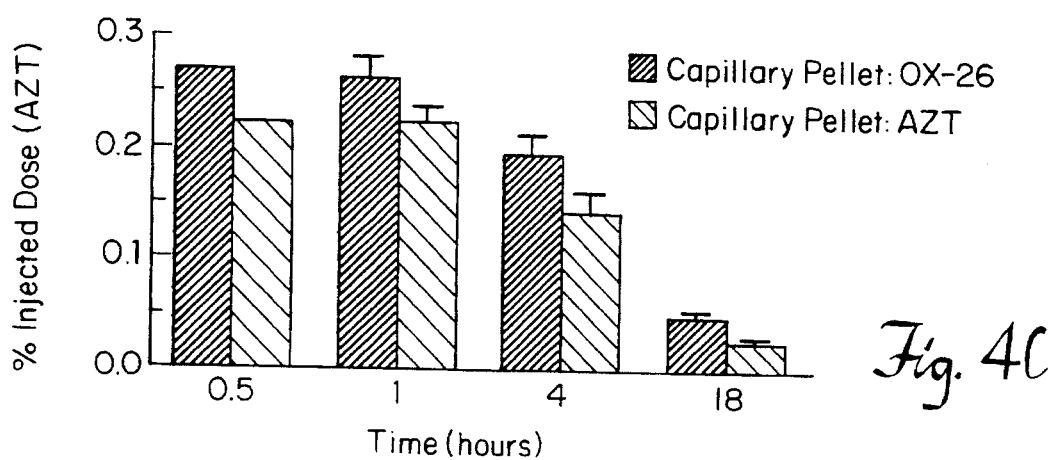

Similar levels of OX-26 and AZT are seen in the capillary fraction of the brain and these levels decrease with time, suggesting that the materials are not being retained by the capillary endothelial cells as illustrated in FIG. 4c. As the levels of OX-26 in the capillary fraction decrease, the levels in the parenchyma fraction increase, indicating that the antibody is migrating from the capillaries to the parenchyma in a time-dependent manner as illustrated in FIG. 4b. In contrast, the levels of AZT in the brain parenchyma do not rise significantly, suggesting that the majority of the drug is released in the endothelial cells and is not transported across the blood-brain barrier. The levels of OX-26 and AZT remained similar in unfractionated homogenates over time as illustrated in FIG. 4a. The data in FIG. 4 are expressed as means±SEM with N=3 rats per time point. These results indicate that the linker is cleaved within the endothelial cells and may represent a method for delivering compounds to those cells.

EXAMPLE 12

Figure 5:
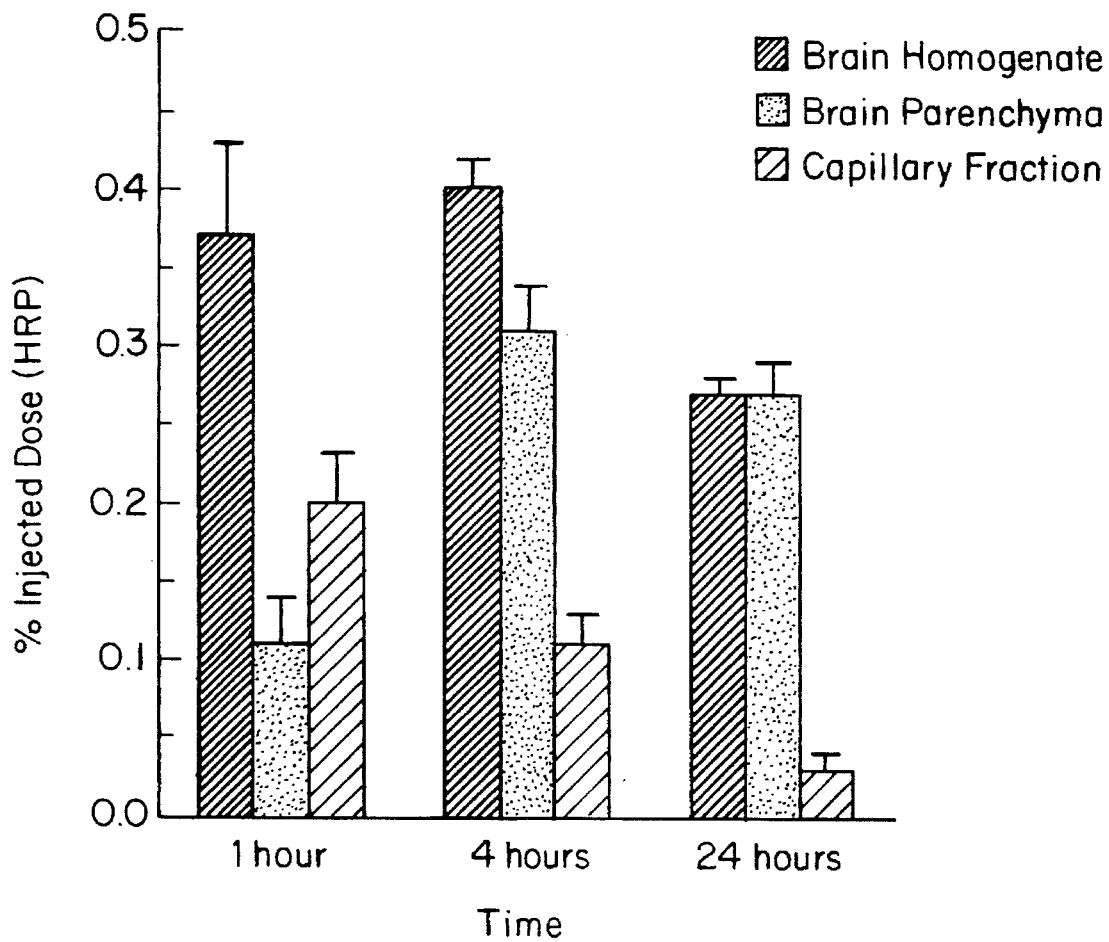
FIG. 5 is a histogram illustrating the experimental results of delivery of a protein, horseradish peroxidase, across the blood-brain barrier in rat brains in the form of a conjugate with OX-26.

Distribution of OX-26-Horseradish. Peroxidase (HRP) in Brain Parenchyma and Capillaries Capillary depletion studies following the procedures described for OX-26 in Example 9 were performed with a $^3$H-labelled OX-26-HRP conjugate that was prepared using a non-cleavable periodate linkage as described in Example 4. The tritium label was distributed between the antibody and the HRP portion of the conjugate. At 1 hour post-injection, the majority of the radioactivity associated with the brain is in the capillary fraction as illustrated in FIG. 5. The data in FIG. 5 are expressed as means±SEM with N=3 rats per time point. By 4 hours post-injection, the distribution of radioactivity associated with the brain changed such that the majority is in the fraction which represents the brain parenchyma. At 24 hours post-injection, essentially all of the $^3$H-labelled OX-26-HRP conjugate is in the parenchyma fraction of the brain indicating that the material has crossed the blood-brain barrier. Similar results were obtained in experiments in which only the HRP portion of the conjugate was radiolabelled.

The percent of injected dose of the OX-26-HRP conjugate that reaches the brain is somewhat lower than that for antibody alone. This is most likely due to the presence of 2 to 3 40 kD HRP molecules attached to each carrier and that these "passenger" molecules are randomly attached to the carrier. Due to this, many of the HRP passengers may be attached to the antibody in such a way as to interfere with antigen recognition. This problem can be alleviated by directing the attachment of the passenger to regions of the carrier removed from critical functional domains.

EXAMPLE 13

Distribution of OX-26-CD4 in Brain Parenchyma and Capillaries

A soluble form of CD4, consisting of amino acids 1–368, was conjugated to OX-26 using a linkage that directed the attachment of the CD4 to the carbohydrate groups located in the Fc portion of the antibody. By directing the site of attachment in this way, the chance that the passenger molecules will interfere with antibody-antigen recongition is lessened. The linkage between the proteins was achieved by first introducing a sulfhydryl group onto CD4 using SATA (N-Succinimidyl S-acetylthioacetate), a commerically available compound. A hydrizid derivative of SPDP, another commercial cross-linking agent, was attached to OX-26 via carbohydrate groups on the antibody. Reaction of the two modified proteins gives rise to a disulfide-linked conjugate.

More specifically the linkage between the proteins was achieved by first introducing a sulfhydryl group onto CD4 using N-succinimidyl S-acetylthioacetate (SATA), a commercially available compound. A 4-fold molar excess of SATA was added to 5 mg of CD4 in 0.1M sodium phosphate buffer containing 3 mM EDTA (pH 7.5). This mixture was reacted at room temperature in the dark for 30 minutes. Unreacted starting materials were removed by passage over a PD-10 column. A hydrizid derivative of SPDP, another commercially available cross-linking agent, was attached to OX-26 via carbohydrate groups on the antibody. Ten milligrams of OX-26 in 2.0 ml of 0.1M sodium acetate, 0.15M sodium chloride (pH 5.0) was reacted with a 1000-fold molar excess of sodium periodate for 1 hour at 4° C. in the dark. Unreacted starting materials were removed by passage over a PD-10 column. The oxidized antibody was reacted with a 30-fold molar excess of hydrazido-SPDP overnight at 4° C. with stirring. Reaction of the two modified proteins gives rise to a disulfide-linked conjugate. One tenth volume of 0.5M hydroxylamine was added to the thioacetylated CD4 (CD4-DATA) and derivatized antibody was then added such that the ratio of CD4 to antibody was 7.5:1. This mixture was reacted at room temperature in the dark for 2 hours. Conjugate was purified by running the reaction mixture over a protein A column followed by a CD4 affinity column.

Figure 6:
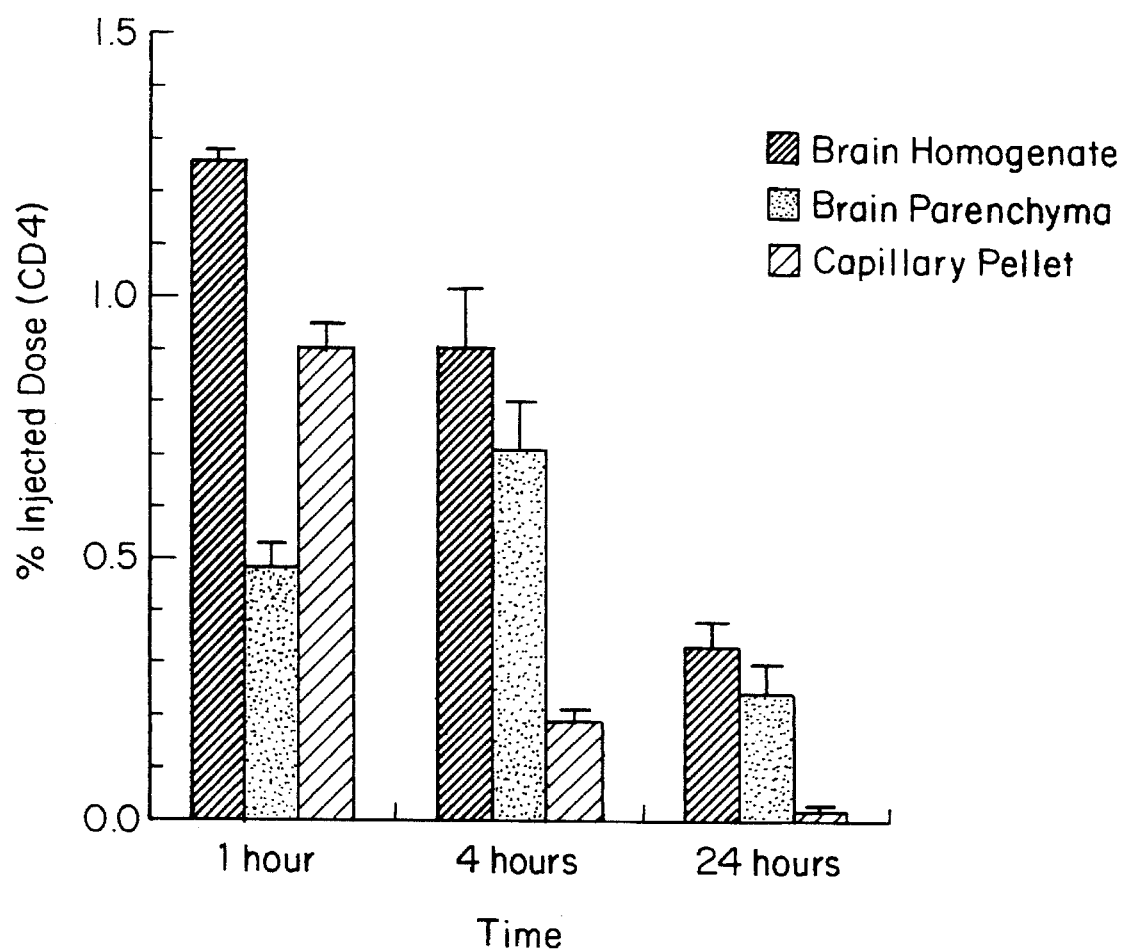
FIG. 6 is a histogram illustrating the experimental results of delivering soluble CD4 to rat brain parenchyma using CD4 in the form of a conjugate with OX-26.

Capillary depletion experiments following the procedures described in Example 9 with OX-26 were performed with an OX-26-CD4 conjugate in which only the CD4 portion was $^3$H-labelled. Time dependent changes in the distribution of the labelled conjugate between the capillary and parenchyma fractions of the brain which are consistent with transcytosis across the blood-brain barrier were observed as illustrated in FIG. 6. The data in FIG. 6 are expressed as means±SEM with N=3 rats per time point.

EXAMPLE 14

Biodistribution and Brain Uptake of Anti-Human Transferrin Receptor Antibodies in Cynomolgous Monkeys A collection of 32 murine monoclonal antibodies which recognize various epitopes on the human transferrin receptor were examined for reactivity with brain capillary endothelial cells in sections from human, monkey (cynomolgous), rat and rabbit brain samples by the immunohistochemical methods described in Example 1. These antibodies were obtained from Dr. Ian Trowbridge of the Salk Institute, LaJolla, Calif. All 32 antibodies displayed some reactivity with human brain endothelial cells. Two antibodies reacted very weakly with rabbit brain capillaries and none reacted with rat. While 21 of the antibodies reacted with monkey brain capillaries, only 2 displayed strong reactivity comparable to that seen with human brain capillaries. These 2 antibodies are herewithin referred to as 128.1 and Z35.2.

Figure 7:
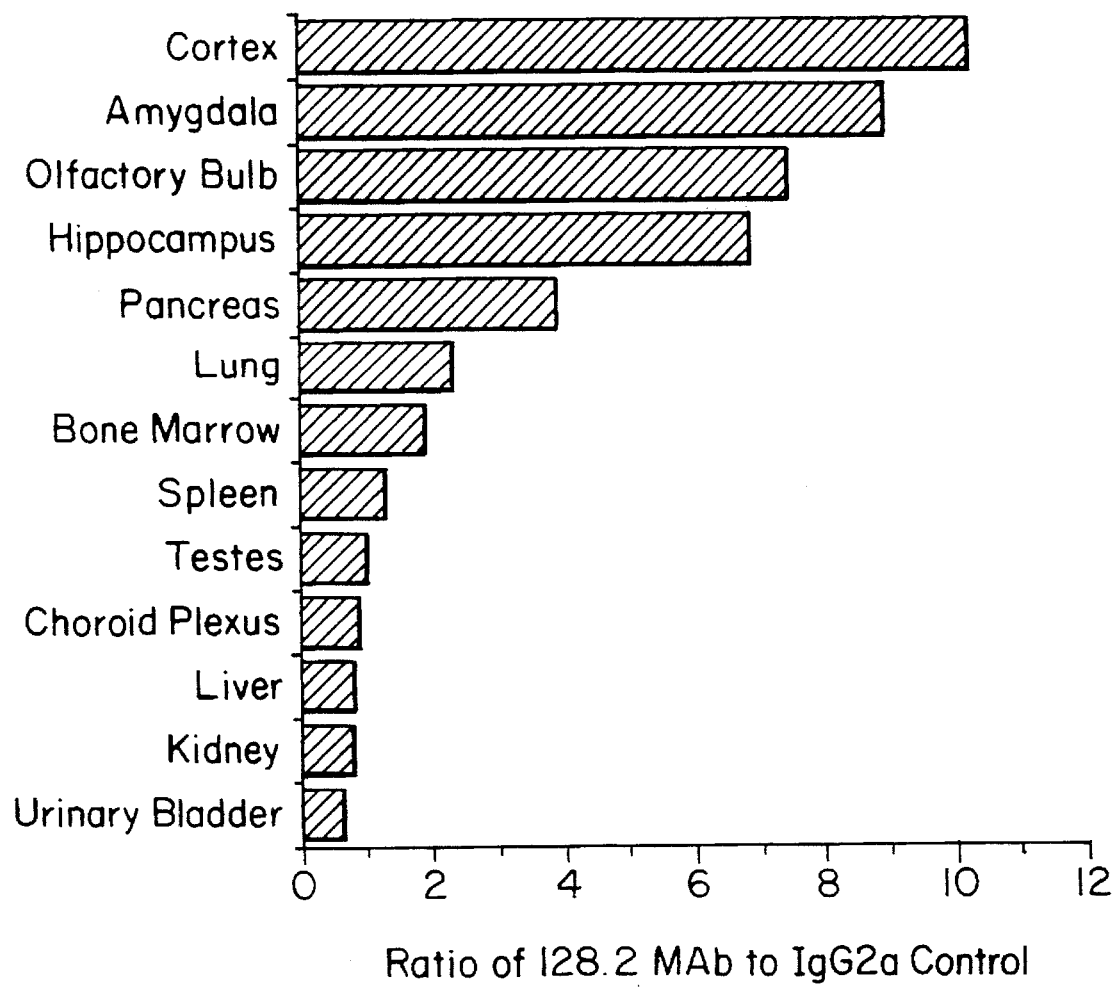
FIG. 7 is a histogram illustrating the biodistribution of antibody 128.1 and control IgG in a cynomolgous monkey.

These antibodies were used to determine the tissue distribution and blood clearance of the $^{14}$C-labelled anti-human transferrin receptor antibodies 128.1 and Z35.2 in 2 male cynomolgous monkeys. 128.1 or Z35.2 was administered concurrently with a $^3$H-labelled control IgG to one of the monkeys with an intravenous catheter. During the course of the study, blood samples were collected to determine the clearance of the antibodies from the circulation. At 24 hours post-injection, the animals were euthanized and selected organs and representative tissues were collected for the determination of isotope distribution and clearance by combustion. In addition, samples from different regions of the brain were processed as described for the capillary depletion experiments in Example 9 to determine whether the antibodies had crossed the blood-brain barrier. The results of the capillary depletion experiments were performed on samples from the cortex, frontal cortex, cerebellum and striatum. All samples had greater than 90% of the 128.1 or Z35.2 in the brain parenchyma, suggesting that the antibodies crossed the blood-brain barrier. The levels of the control antibody in the same samples were from 5 to 10-fold lower. Using the average brain homogenate value for dpm/G tissue, the percent injected dose of 128.1 in the whole brain is approximately 0.2–0.3%. This compares to a value of 0.3–0.5% for OX-26 in the rat at 24 hours post-injection. A comparison of the ratios of 128.1 to the control antibody for various organs is illustrated in FIG. 7. Similar results were obtained for Z35.2. These results suggest that 128.1 is preferentially taken up by the brain as compared to control antibody. For the majority of organs and tissues tested, the ratio of 128.1 to control is less than 2.

EXAMPLE 15

Delivery of Nerve Growth Factor to the Brain via Anti-Transferrin Receptor Antibodies and Antibody Fragments Nerve growth factor (NGF) is a 26,000 dalton protein which has been shown in vitro and in vivo to support the growth of basal forebrain cholinergic neurons. In Alzheimer's Disease, these cells undergo significant degenerative changes which, at least in part, may be responsible for some of the cognitive and memory deficits that are associated with this disorder. Because of this correlation, NGF has been proposed as a potential therapeutic agent for the treatment of Alzheimer's Disease. The studies described below demonstrate the ability of OX-26 to deliver NGF across the blood-brain barrier.

CONJUGATE SYNTHESIS AND PURIFICATION

The following procedure was followed for producing conjugates of NGF to the OX-26 antibody or its Fab or F(ab')$_2$ fragments.

NGF was conjugated to the OX-26 antibody through a disulfide bond. NGF was modified through its carboxyl groups with EDC (1-Ethyl-3-(3-dimethylaminopropyl)carbodiimide) and PDP (pyridyldithiopropionate)-hydrazide to introduce a thiol-reactive pyridyldithio group. OX-26 was modified through its lysine amines with SATA (see Example 13) to introduce a protected sulfhydryl group for subsequent reaction to form the disulfide bonds. The extent of protein modification was monitored and the reaction conditions were such that the number of groups attached to both the antibody and NGF was kept to a minimum (approximately 5 and 1, respectively). Conjugates were prepared by reacting derivatized NGF with the deprotected OX-26 at a 7.5:1 molar ratio. The reactions were run under nitrogen in 0.1M sodium phosphate/3 mM EDTA, pH 7.5 at room temperature for 2 hours. The free sulfhydryl group on the OX-26 exchanges with the 2-pyridyl-sulfide group on NGF, forming a disulfide bond between the two proteins and releasing pyridine-2-thione. In general, these reaction conditions generated a 1:1 to 1:2 (OX-26:NGF) conjugate with a yield (in terms of NGF) of between 20 and 30%.

Purification of these conjugates from unreacted starting materials was initiated by passage over a Protein-A Sepharose column to remove unreacted NGF. The material eluted from this column, which consisted of conjugate and free antibody, was then passed over a NGF affinity column. Free OX-26 flowed through this column whereas OX-26-NGF conjugate was retained.

The purity of the conjugate eluted from the NGF affinity column was assayed using SDS-PAGE under reducing and nonreducing conditions. Conjugate formation was verified by ELISA and, on occasion, by immunoblot or autoradiography as well. The activity of the NGF portion of the conjugate was verified by using the PC-12 neurite outgrowth assay. Typically, the conjugate activity was within one dilution of the NGF standard.

BRAIN TARGETING AND DELIVERY

The targeting of the antibody-NGF conjugate to the brain capillaries was assessed using immunohistochemistry as described in Example 1. An antimouse IgG antisera was used to localize the OX-26 portion of the conjugate while an anti-NGF antibody was used to localize the "passenger" protein. Both proteins were detected in the vasculature of the brain following iv administration of OX-26-NGF conjugate; NGF was not detected when injected as a free protein. That is, NGF was detected in the vasculature of the brain only when it was administered in the form of a covalent conjugate with OX-26. In addition, the attachment of NGF to OX-26 did not significantly alter the targeting of the antibody to the brain capillaries.

The delivery function of the anti-TfR portion of the conjugate was quantitated using the capillary depletion procedure as described in Example 9. For these studies, NGF was radiolabeled with $^3$H prior to conjugation. The results indicated that approximately 0.5% of the injected dose of NGF crossed the blood-brain barrier and accumulated in the brain parenchyma when the NGF was conjugated to intact OX-26 antibody. When NGF was conjugated to OX-26 Fab fragments, approximately 0.15% of the injected dose of NGF crossed the blood-brain barrier and accumulated in the brain parenchyma. When NGF was conjugated to OX-26 F(ab')$_2$ fragments, between 0.1% and 0.2% of the injected dose of NGF reached the brain parenchyma after passing across the blood-brain barrier.

BRAIN UPTAKE OF OX-26-NGF

Quantitative uptake into the brain of the OX-26-NGF conjugate over a short-term time course was measured. These measurements demonstrated the passage of the conjugate across the blood-brain barrier.

The measurements were performed by a capillary depletion procedure similar to that described in Example 9. In this procedure, a two-site immunoassay (EIA) for NGF was used. After dissection, the brain samples were frozen on dry ice, homogenized and centrifuged, and the supernatants taken for EIA. Immunoplates were coated with monoclonal anti-mouse-β-NGF antibodies 27/21 (0.5 ug/ml, Boehringer-Mannheim). Control wells were coated with the same amount of control mouse IgG. The dishes were incubated with the samples at 4° C. overnight. As standards, samples of purified mouse NGF were used. After extensive wash, 27/21-β-galactosidase conjugate antibodies were applied overnight (Boehringer, 4 units of enzyme activity/ml). Enzyme activity was measured in a microplate fluorometer (Dynatech Microfluor) and the NGF concentration in brain samples determined by comparison with the regression line of the NGF standards. Statistical analysis was carried out using analysis of variance in a general linear model (GLM) with repeated measures or comparing small series of values with a Mann-Whitney U-test.

Figure 8:
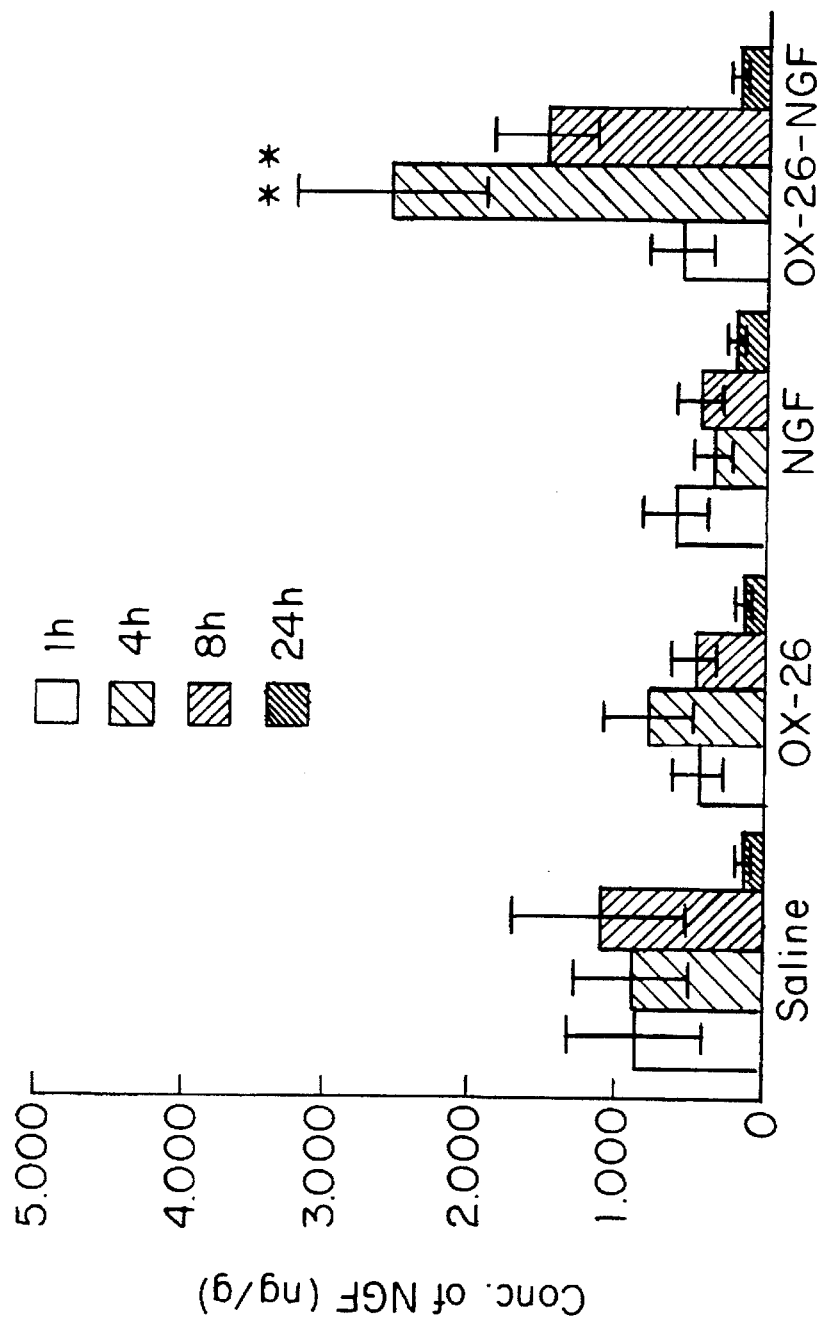
FIG. 8 is a histogram illustrating the uptake of NGF delivered as a conjugate with OX-26 into the cerebellum.

Quantitative uptake into the brain was followed in the cerebellum, which is a region of the brain with a low endogenous level of NGF, thereby facilitating detection of the extra contribution from the injected conjugate. For comparison, the uptake of injected NGF in the submandibular gland of the rat was followed as representing a peripheral organ outside the BBB. As can be seen in FIG. 8, the levels of NGF were significantly increased in cerebellar tissue 4–8 hours following intravenous injection of OX-26-NGF, but not OX-26, saline or NGF alone. These results indicate that it takes some time for the OX-26-NGF conjugate to clear from the vascular wall, and to be taken up by the brain tissue (compare the levels at 1 hour postinjection). Also, it is clearly shown in this figure that equimolar injection of NGF alone did not result in any significant uptake of NGF into the cerebellum.

FIMBRIA FORNIX LESION MODEL

Cholinergic neurons, which are localized in the nucleus basalis of Meynert and the medial septal nucleus, innervate the neocortex, hippocampus and amygdala in response to the NGF produced by these postsynaptic target areas. It has been shown in rats that if the supply of NGF is interrupted by transection of the fimbria fornix, which results in a lesion in the septo-hippocampal pathway, the cholinergic neurons in the basal forebrain will degenerate. If exogenous NGF is administered by intracerebroventricular (icv) infusion to the lesioned animals, the atrophy by cholinergic neurons can be prevented. (Williams et al., "Continuous Infusion of Nerve Growth Factor Prevents Basal Forebrain Neuronal Death after Fimbria Fornix Transaction", *PNAS* 83, 9231–9235 (1986)).

This model system was used to examine the efficacy of NGF delivered iv using an anti-TfR antibody. The treatment groups in this experiment consisted of OX-26-NGF iv, NGF iv, OX-26 iv, NGF icv and carrier buffer icy. The iv dosing regimen consisted of 30 μg NGF, either as conjugate or free protein, or an amount of OX-26 equivalent to that in the conjugate, given daily for two weeks. Based on the percent of the injected dose of NGF that reaches the brain parenchyma as determined from the capillary depletion experiments, this dose of conjugate should result in the delivery of approximately 2.0 μg of NGF. Taking into account the $K_D$ of the NGF receptor, this amount of NGF should be more than sufficient to stimulate the cholinergic neurons of the basal forebrain if the NGF is transported intact across the blood-brain barrier. The icv animals were treated via cannulas attached to Alzet osmotic minipumps.

At the completion of the dosing period, the animals were perfused and the brains removed for histochemical analysis. Acetylcholinesterase (ACHE) histochemistry was used to verify the completeness of the lesion. Immunohistochemical staining using an antibody to the low affinity NGF receptor (LNGFR or P75) was used to visualize the cholinergic neurons in the basal forebrain. Neurons on the ipsilateral side of the lesion atrophy due to a lack of NGF. The results were scored by counting the number of neurons remaining on the lesioned (ipsilateral) side of the brain relative to the number on the unlesioned (contralateral) side. Typically between 50–60% of the neurons on the lesioned side of the brain degenerate without an exogenous source of NGF.

The results of this experiment are shown in Table 1.

TABLE I

Results of Fimbria Fornix Experiment #1

| Treatment | Result (% stained neurons, ipsilateral/contralateral) |
|---|---|
| NGF iv | 41.5 ± 8.3 |
| carrier buffer icv | 50.0 ± 10.5 |
| AK-26-NGF conjugate iv (#1) | 60.8 ± 19 |
| AK-26-NGF conjugate iv (#2) | 96.5 ± 32 |
| AK-26-NGF conjugate iv (#3) | 85.9 ± 14 |

In the two negative control animals that had complete lesions (1 NGF iv and 1 carrier buffer icv), approximately 40–50% of the neurons on the ipsilateral side of the lesion survived relative to those on the contralateral side of the lesion. In contrast, the percent of neurons surviving in two of the conjugate-treated animals was ~80–90%; this is as good as, if not better than, what has been reported for NGF treatment icv. A third conjugate treated animal showed ~60% neuron survival, which was less than that for the other two animals but still better than the negative controls.

EXAMPLE 16

Delivery of Nerve Growth Factor to Intraocular Implants via Anti-Transferrin Receptor Antibodies Another method for analyzing the ability of the anti-TfR antibodies to deliver active NGF across the blood-brain barrier is to examine the effect of OX-26-NGF conjugates on fetal medial septal nucleus tissue that has been implanted into the anterior chamber of the eye. This system provides a means for studying the effects of NGF on the developing cholinergic neurons in the medial septal nucleus that has been isolated from other CNS influences. An advantage of this system is that cholinergic neurons in fetal tissue are much more sensitive to NGF than are those in adult tissue.

To demonstrate the usefulness of this system for the study of NGF delivery via the anti-rat TfR antibody, preliminary immunohistochemistry experiments were performed to examine the localization of the antibody in the tissue grafts. The results of these studies indicated that OX-26 targets to the vasculature of the implants in a manner indistinguishable from that seen in the host brain.

In this experiment, 2 mm³ pieces of medial septal nucleus tissue were dissected from rat fetuses at gestational day E18 and bilaterally grafted to the anterior chamber of the eye of adult rats (2 groups of 6 animals each). NGF treatment was not begun until two weeks after grafting to allow vascularization of the implants and formation of a vascular equivalent of the blood-brain barrier. The dose of conjugate that was administered was calculated based on the size of the target tissue the percent of the injected dose of the conjugate NGF which crosses the blood-brain barrier and the $K_d$ of the NGF receptor for NGF. These calculations resulted in a dose/injection of ~12 μg NGF. In keeping with previous experiments which examined the effects of intraocularly administered NGF on implants in the anterior chamber of the eye, the initial dosage regimen involved iv bolus injections of conjugate or control every two weeks over a period of 8 weeks. During this time period, the effect of the conjugate-derived NGF on the growth of the tissue implants was monitored by weekly observations through the cornea of the living host using a stereo-microscope equipped with an eyepiece micrometer.

Figure 9:
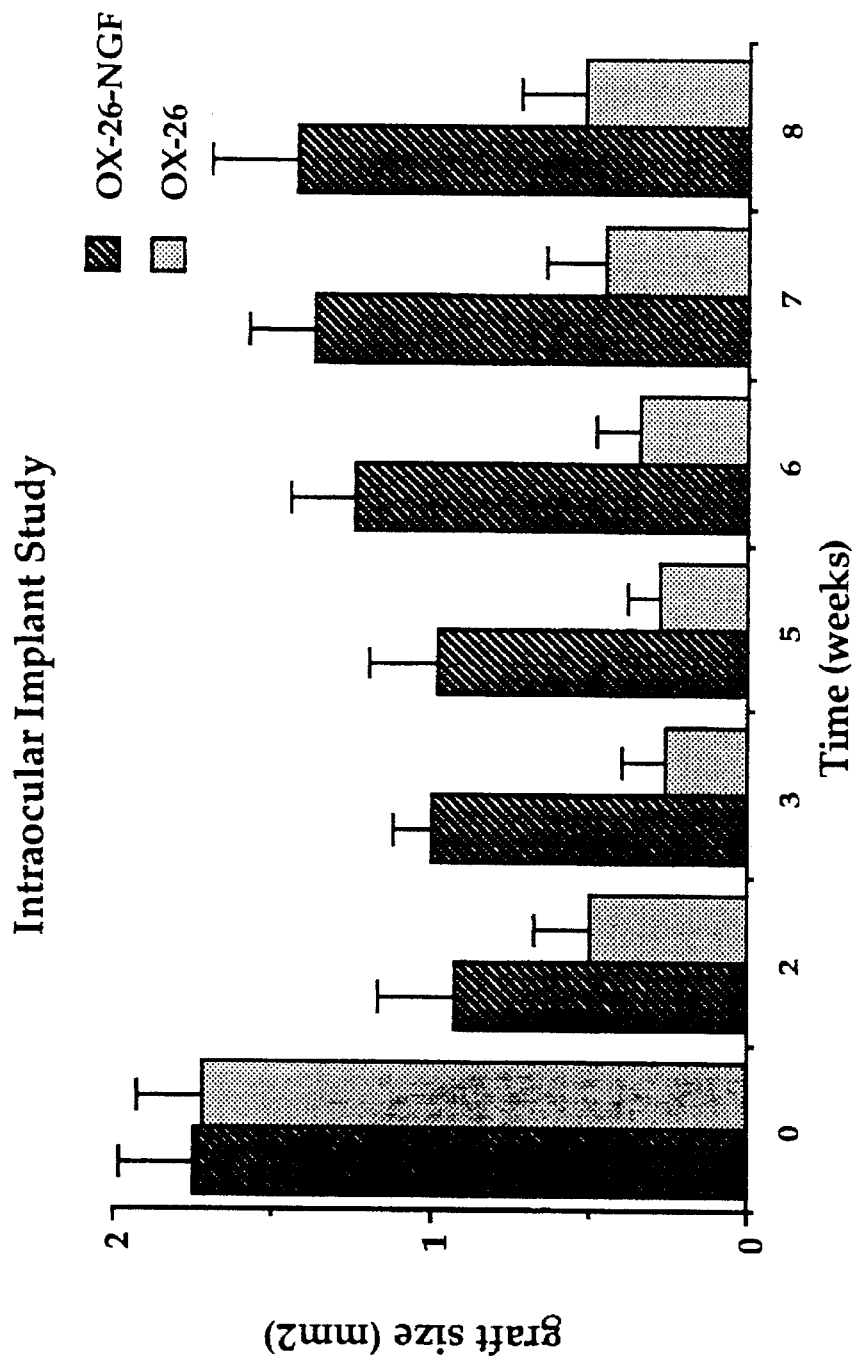
FIG. 9 is a histogram illustrating the effects of NGF delivered as a conjugate with OX-26 on the graft size of intraocular inplants.

The results of the implant growth studies are shown in FIG. 9. During the 2 weeks prior to the first treatment, the size of the implants decreased steadily. Coincident with the first treatment, the two groups diverged with the OX-26-NGF conjugate-treated implants stabilizing in size and the OX-26-treated implants continuing to decrease in size. In addition, the conjugate-treated grafts appeared to increase in size after the 6 week injection. These results suggest that the NGF delivered by the conjugate sustains the cholinergic neurons in the graft, thus leading to the increased graft size relative to the control.

At the completion of the dosing period, the animals were sacrificed sad the tissue fixed, sectioned and processed for ChAT-immunostaining to identify cholinergic cells; it had been shown previously that intraocular administration of NGF can increase the number of ChAT-positive cells in basal forebrain tissue grafts by approximately 80% over that observed in untreated control grafts. The results from the grafts taken from OX-26 treated animals indicated little or no staining for ChAT in this tissue, suggesting that few, if any, cholinergic neurons had survived. In contrast, grafts taken from OX-26-NGF treated animals showed very intense ChAT staining with many ChAT positive cells clearly visible. These results support tire results of the implant growth measurements anal indicate that the conjugate is able to deliver active NGF to the tissue grafts, which possess a vascular equivalent to an intact blood-brain barrier.

Despite the marked differences in overall graft sizes, histological examination of the septal transplants showed no obvious differences in the density of neural or glial structures within the two groups of grafts. Specifically, the density of cells and the vascularization of grafts in the two groups appeared to be the same. To specifically investigate the survival of septal cholinergic neurons in the transplants, the CHAT-immunohistochemistry was used to reliably visualize cholinergic structures in nervous tissue. A much larger number of cholinergic neurons, approximately a three and a half-fold increase, was found in the group of transplants injected with OX-26-NGF as compared to the control group. Because the transplants in the NGF conjugate groups were significantly larger, the total numbers of both cholinergic and non-cholinergic neurons surviving were larger than in the control groups, a finding in keeping with previous studies that made use of intraocular injections of NGF. These results further support the concept that NGF passed through the blood-brain barrier into the grafts and enhanced the survival of cholinergic neurons in the groups injected with the NGF conjugate. These results also indicate that NGF passed through the blood-brain barrier into the grafts and enhanced the survival of non-cholinergic neurons, perhaps by indirect or accessary processes, in the groups injected with the NGF conjugate.

EXAMPLE 17

Formation of Anti-Transferrin Receptor Antibody Conjugates with Superoxide Dismutase Which Retain Enzyme Activity Superoxide dismutase (SOD), a 32,000 dalton protein, scavenges superoxide free radicals by converting them to hydrogen peroxide and molecular oxygen. It has been shown that superoxide radicals, which are produced during ischemia and reperfusion, alter endothelial cell and blood-brain barrier permeability and elicit brain edema and cellular injury through lipid peroxidation. The primary difficulties associated with using SOD as a therapeutic for stroke have heretofore been its short serum half-life and poor localization at the site of damage.

CONJUGATE SYNTHESIS AND PURIFICATION

Conjugation of superoxide dismutase (SOD) to OX-26 was performed following the strategy previously described for CD4 (see Example 13). SOD was modified with SATA to introduce a protected thiol group and OX-26 was modified through the carbohydrate group with PDP-hydrazide to yield a disulfied-linked conjugate. The yield of conjugate with this approach was approximately 10% (in terms of SOD).

Purification of the conjugate from unreacted SOD was achieved by passing the material over a gel filtration column. Chromatography on a Mono S column (a cation exchanger) separated the free SOD and some of the free antibody from the conjugates. This was accomplished by recovering only the leading edge of the antibody elution from the column. Approximately a 50:50 mixture of conjugate and free antibody was obtained. OX-26-SOD conjugate synthesis was verified by immunoblot and by ELISA.

The activity of SOD after conjugation was measured using a dye reduction assay. When riboflavin is photochemically reduced and then re-oxidized through exposure to air, superoxide radicals are produced. These radicals then reduce nitroblue tetrazolium dye to a blue color. The assay measures the ability of SOD to inhibit the reduction of the dye by removing the superoxide radicals. It was found that the recovered OX-26-SOD conjugates retained greater than 60% of the SOD activity.

EXAMPLE 18

Formation of Anti-Transferrin Receptor Antibody Conjugate with Anti-Amyloid Antibody Anti-amyloid antibodies or antibody fragments immunoreactively bind with amyloid plaques that are characteristic of Alzheimer's Disease. For clinical diagnostic detection purposes, a detectable group such as gadolinium or technitium is often attached to the anti-amyloid antibody. This allows imaging of the brain to be performed. Heretofore, it has been difficult to easily deliver a diagnostically useful amount of the anti-amyloid antibodies past the blood-brain barrier.

CONJUGATE SYNTHESIS AND PURIFICATION

The two antibodies (OX-26 and 10H3) were joined together using SATA and SPDP to form a disulfide linkage following procedures described previously (Example 13). The conjugate (approximately 1:1) was purified from free antibody on a gel filtration column. Some of this conjugate was tested both by slot-blots and ELISA for binding to the amyloid peptide used to produce the antibody. The antigen binding activity of the conjugate was as good as, if not better than, the unconjugated antibody; this indicated that the 10H3 antibody was not affected by the conjugation process. In addition, the conjugate was injected into a rat and immunohistochemistry was used to examine targeting to the brain vasculature via the anti-transferrin receptor antibody. The conjugate was localized to the brain vasculature in a manner similar to that for OX-26 alone, indicating that the attachment of this anti-amyloid antibody to OX-26 did not affect its ability to target to brain capillary endothelial cells in vivo Equivalents Those skilled in the art will know, or be able to ascertain using no more than routine experimentation, many equivalents to the specific embodiments expressly described herein. These are intended to be within the scope of the invention as described by the claims herein.

I claim:

1. A method for delivering a therapeutically effective amount of a nerve growth factor or a neurotrophic factor across the blood-brain barrier of a mammal comprising administering a conjugate of an antibody, or biologically functional binding fragment thereof, and either a nerve growth factor or a neurotrophic factor to the mammal under conditions whereby said conjugate binds to transferrin receptors on brain endothelial cells and the nerve growth factor or the neurotrophic factor is transported across the blood-brain barrier of the mammal in a pharmaceutically active form and in a therapeutically effective amount.

2. A method of claim 1 wherein the neurotrophic factor is selected from the group consisting of ciliary neurotrophic factor, brain-derived neurotrophic factor, neurotrophin 3, neurotrophin 4 and neurotrophin 5.

3. A method of claim 1 wherein said antibody comprises a monoclonal antibody.

4. A conjugate of an antibody, or biologically functional binding fragment thereof, and either a nerve growth factor or a neurotrophic factor wherein said conjugate is bindable to transferrin receptors on brain endothelial cells.

5. A conjugate of claim 4 wherein the neurotrophic factor is selected from the group consisting of ciliary neurotrophic factor, brain-derived neurotrophic factor, neurotrophin 3, neurotrophin 4 and neurotrophin 5.

6. A conjugate of claim 4 wherein said antibody comprises a monoclonal antibody.

7. A pharmaceutical composition comprising: (a) a conjugate of an antibody, or biologically functional binding fragment thereof, and either a nerve growth factor or a neurotrophic factor, and (b) a pharmaceutically acceptable carrier, wherein said conjugate is bindable to transferrin receptors on brain endothelial cells.

8. A composition of claim 7 wherein the neurotrophic factor is selected from the group consisting of ciliary neurotrophic factor, brain-derived neurotrophic factor, neurotrophin 3, neurotrophin 4 and neurotrophin 5.

9. A composition of claim 1 wherein said antibody portion comprises a monoclonal antibody.

* * * * *

UNITED STATES PATENT AND TRADEMARK OFFICE
CERTIFICATE OF CORRECTION

PATENT NO. : 5,527,527
DATED : June 18, 1996
INVENTOR(S) : Phillip M. Friden

It is certified that error appears in the above-indentified patent and that said Letters Patent is hereby corrected as shown below:

Column 24, line 57: Delete "claim 1" and insert therefor --claim 7--.

Signed and Sealed this

Seventeenth Day of September, 1996

Attest:

BRUCE LEHMAN

Attesting Officer

Commissioner of Patents and Trademarks